US007527597B2

(12) United States Patent
Sandler et al.

(10) Patent No.: US 7,527,597 B2
(45) Date of Patent: May 5, 2009

(54) ACOUSTIC DETECTION OF VASCULAR CONDITIONS

(75) Inventors: Richard H. Sandler, Evanston, IL (US); Hansen A. Mansy, Justice, IL (US)

(73) Assignee: Biomedical Acoustic Research Corporation, Evanston, IL (US)

( * ) Notice: Subject to any disclaimer, the term of this patent is extended or adjusted under 35 U.S.C. 154(b) by 815 days.

(21) Appl. No.: 10/817,064

(22) Filed: Apr. 2, 2004

(65) Prior Publication Data

US 2004/0249293 A1 Dec. 9, 2004

Related U.S. Application Data

(63) Continuation-in-part of application No. 10/046,863, filed on Jan. 15, 2002, now Pat. No. 6,780,159.

(60) Provisional application No. 60/261,997, filed on Jan. 16, 2001.

(51) Int. Cl.
*A61B 5/00* (2006.01)
(52) U.S. Cl. .............................. 600/504; 600/586
(58) Field of Classification Search ............... None
See application file for complete search history.

(56) References Cited

U.S. PATENT DOCUMENTS 5,036,857 A * 8/1991 Semmlow et al. ........... 600/528
5,311,867 A * 5/1994 Kynor ....................... 600/409
5,638,823 A * 6/1997 Akay et al. ................. 600/528
6,278,890 B1 * 8/2001 Chassaing et al. ........... 600/407
6,692,443 B2 * 2/2004 Crutchfield et al. ......... 600/504
7,291,111 B2 * 11/2007 Shertukde et al. ........... 600/483

OTHER PUBLICATIONS

Mansy, Hoxie, Patel, Sandler, "Computerised analysis of auscultatory sounds associated with vascular patency of haemodialysis access," Medical & Biological Engineering & Computing 2005, Jul. 28, 2004, 7 pages, vol. 43.

* cited by examiner

*Primary Examiner*—Robert L Nasser
(74) *Attorney, Agent, or Firm*—Hanley, Flight, & Zimmerman, LLC

(57) ABSTRACT

Apparatus and methods that use the acoustic characteristics of vascular blood flow to assess vascular conditions are disclosed. An example method for detecting a change in a vascular condition receives sound information associated with blood flowing through a vascular structure and converts the sound information into data associated with a plurality of cardiac cycles. The example method processes the data associated with the plurality of cardiac cycles to determine an acoustic characteristic associated with a current state of the vascular condition and detects the change in the vascular condition based on a difference between the acoustic characteristic associated with the current state of the vascular condition and a baseline acoustic characteristic associated with an earlier state of the vascular condition.

45 Claims, 15 Drawing Sheets

ACOUSTIC DETECTION OF VASCULAR CONDITIONS

RELATED APPLICATIONS

This application is a continuation-in-part of U.S. patent application Ser. No. 10/046,863 filed on Jan. 15, 2002 now U.S. Pat. No. 6,780,159, which claims the benefit of the filing date of U.S. Provisional Patent Application No. 60/261,997 filed on Jan. 16, 2001.

FIELD OF THE DISCLOSURE

The present disclosure relates generally to the non-invasive diagnosis of conditions within a human or animal body and, more particularly, to apparatus and methods that use the acoustic characteristics of vascular blood flow to assess vascular conditions.

BACKGROUND

Assessment of vascular (i.e., artery and vein) conditions is crucial to the diagnosis of many serious, and often life threatening, pathologies. For example, vascular occlusions, which commonly take the form of atherosclerotic vessel disease, can reduce or eliminate the flow of blood to critical organs within a body, thereby causing illness, disability and/or death. In particular, one or both of the carotid arteries supplying blood to the brain may become blocked and cause what is commonly referred to as a stroke. As is well known, a stroke often results in lasting disability and can result in death. Further, portions of the aorta, which is a major artery within the body that conveys blood from the heart to organs throughout the body, may become diseased, particularly in the abdominal region. A diseased aorta can cause severe pain and may eventually form an aneurysm that ruptures and causes death. Still further, femoral and popliteal arteries may become blocked. Typically, blockages in the femoral and popliteal arteries form near the groin and legs and cause weakness in the legs. If these blockages in the femoral and popliteal arteries are not diagnosed and treated in a timely manner, amputation of one or both legs may be required. Still further, the renal arteries, which convey blood from the abdominal aorta to the kidneys, may become blocked, thereby causing hypertension, kidney failure and ultimately death.

One particularly problematic vascular condition occurs in patients that have chronic renal (i.e., kidney related) failure. As is well known, renal dialysis and vascular access to carry out the dialysis are critical aspects of managing chronic renal failure. In fact, without some form of dialysis, the more than 120,000 people in the United States with chronic renal failure would rapidly succumb to their disease.

Hemodialysis is the most commonly employed renal dialysis technique. To effectively carry out hemodialysis, large needles must be inserted into large blood vessels so that substantial quantities of blood can be processed by the dialysis equipment in a relatively short period of time. Additionally, because hemodialysis must typically be performed several times each week for months or possibly years, arterial-venous (AV) access shunts are needed to provide long-term vascular access. As is well known, an AV shunt is disposed between an artery and a vein, usually located in the patient's forearm, to enable blood to flow directly between the artery and the vein. The AV shunt provides the large blood vessel that is needed to accommodate the relatively large dialysis needle and bypasses high resistance vessels such as arterioles and capillaries to facilitate the high blood flow rates needed to accomplish efficient hemodialysis. In practice, an AV shunt may be created by surgically placing a graft, which is typically either made of an artificial material or scavenged from a vessel in another location of the body such as, for example, the leg. Alternatively, the AV shunt may be a fistula, which is created using direct anastomosis of an artery and a vein.

While the above-described AV shunts initially function properly, these AV shunts typically become clogged (with blood clots, for example, which may be caused by hyperplasia) over time. Furthermore, although there are a variety of techniques which can be used to treat (i.e., eliminate or reduce) vascular blockages such as, for example, angioplasty, early diagnosis of the blockage is needed to minimize risk to the patient and to maximize the likelihood that treatment will successfully reduce the blockage to a safe level or eliminate the blockage completely.

Further, due to the limited number of areas on a patient's body which may be used for hemodialysis access, it is crucial that access sites are preserved as long as possible. AV grafts account for about 75% of dialysis access devices and over one-half of these AV grafts require angioplastic or other salvage intervention within the first year. With AV fistulas, on the other hand, about 30% are unusable due to a failure to mature. Additionally, of the AV fistulas that successfully mature, about 15% require radiologic or surgical revision within one year.

At present, physical examination is a commonly used technique for assessment of vascular patency. Physical examination techniques are particularly useful for detecting very low blood flow which, in the case of an AV shunt, is indicative of an impending shunt failure. As is well known, vascular flux pulse and thrill (i.e., a vascular murmur) and auscultation may be used to assess vascular patency. Generally speaking, a palpable murmur or thrill is indicative of a reasonable blood flow (e.g., greater than about 450 milliliters/minute), a sharp pulse indicates lower blood flows and an increased bruit (i.e., an abnormal sound) suggests a vascular stricture or stenosis.

Longitudinal monitoring of blood flow is another well-known technique for detecting significant vascular stenosis. However, longitudinal monitoring techniques are less desirable in practice because these techniques require standardization of tubing size, needle size and other hemodialysis equipment. Still further, duplex color Doppler ultrasound flow studies, dilution and magnetic resonance imaging are other well-known techniques for assessing vascular patency. Unfortunately, these well-known techniques are relatively expensive, of limited availability, and the results obtained with these techniques depend heavily on the skill level of the observer.

SUMMARY

Example acoustic detection methods, apparatus and articles of manufacture disclosed herein enable the non-invasive assessment of vascular conditions within a human or animal body. Generally speaking, the acoustic detection methods and apparatus disclosed herein measure vibrations or sounds generated by blood flowing through shunts, arteries and/or veins and process these measured vibrations or sounds to diagnose the internal condition of the shunts, arteries and/or veins. In particular, the acoustic detection methods and apparatus disclosed herein may be used to assess vascular patency in, for example, an AV shunt that provides vascular access for dialysis procedures. Thus, the acoustic detection methods, apparatus and articles of manufacture disclosed herein may be used to determine if a critical AV shunt has failed or is near failure, thereby reducing the possibility that a dialysis patient will be subjected to a life threatening condition.

More generally, the acoustic detection methods and apparatus disclosed herein may be used in a variety of applications in which non-invasive assessment of vascular conditions is desired. For example, the acoustic detection methods and apparatus may be used to locate a vascular blockage and to assess the degree of the blockage. In particular, the acoustic detection methods and apparatus may be used to detect blockages in carotid arteries to help prevent strokes, may be used to detect stenosis within renal arteries, may be used for early detection of abdominal aortic aneurysms, may be used to facilitate salvage of a femoral-popliteal bypass graft, etc.

DETAILED DESCRIPTION

Generally speaking, the example apparatus, methods and articles of manufacture disclosed herein may be used to acoustically detect vascular conditions. More specifically, the example acoustic detection methods and apparatus disclosed herein may be used to detect vibrations or sounds imparted by blood flow to shunt, artery and/or vein walls. Sensors placed near or on the skin surface may then be used to convert these flow-induced vascular vibrations or sounds into electrical signals that are subsequently processed to determine the conditions within the underlying vascular structure(s). The electrical signals may be processed to generate temporal and/or spectral information that may be indicative of a condition such as, for example, the patency within a vascular structure. For instance, the temporal and/or spectral information generated using the methods and apparatus disclosed herein may be used to assess the condition of an AV shunt that is used for renal dialysis by comparing the generated temporal and/or spectral information to reference temporal and/or spectral information which is associated with a predetermined normal or acceptable vascular condition and/or a baseline condition associated with a particular subject or patient. Thus, the acoustic detection methods and apparatus disclosed herein may be used to non-invasively determine if vascular compromise, or any other vascular abnormality, is present.

While the example acoustic detection methods and apparatus are specifically described herein in connection with the assessment of vascular patency within an AV shunt, the disclosed methods and apparatus are more generally applicable to a wide variety of applications and may be used to detect abnormalities such as, for example, occlusions or stenoses within veins or arteries that carry blood to any organ or any other portion of a body. For example, the acoustic detection methods and apparatus disclosed herein may be used to detect compromise (e.g., an occlusion or stenosis) within one or more of the carotid arteries, thereby enabling medical professionals to take measures to prevent a stroke.

Figure 1:
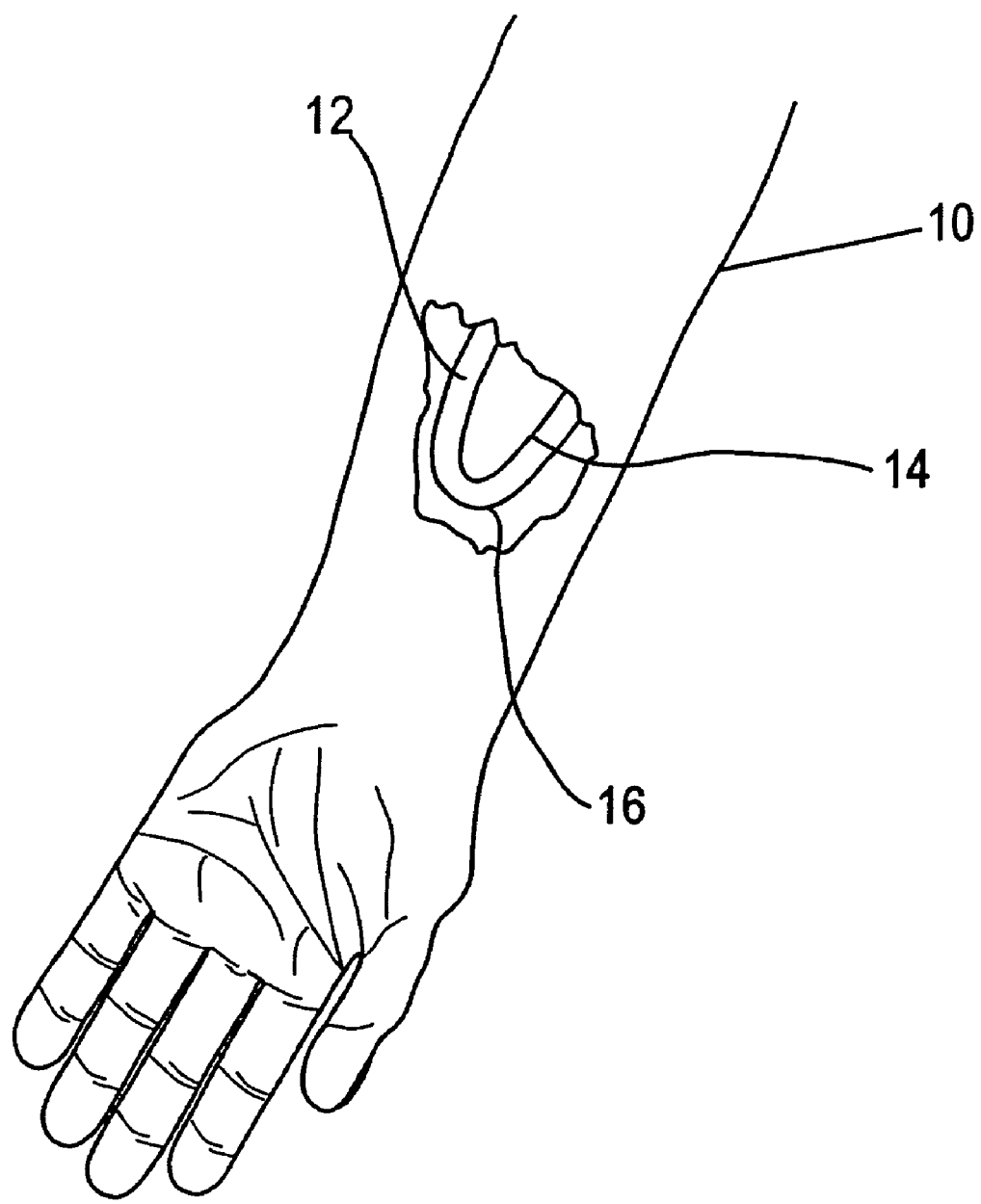
FIG. 1 is an exemplary diagrammatic cut-away view of a human forearm that illustrates the vascular anatomy for a typical renal dialysis arterio-venous (AV) shunt.

FIG. 1 is an exemplary diagrammatic cut-away view of a human forearm 10 that illustrates the vascular anatomy for a typical renal dialysis AV shunt. As shown in FIG. 1 by way of example only, an artery 12 and a vein 14 are connected to one another via a shunt 16 which, as described above, may be implemented using a graft or a fistula.

Figure 2:
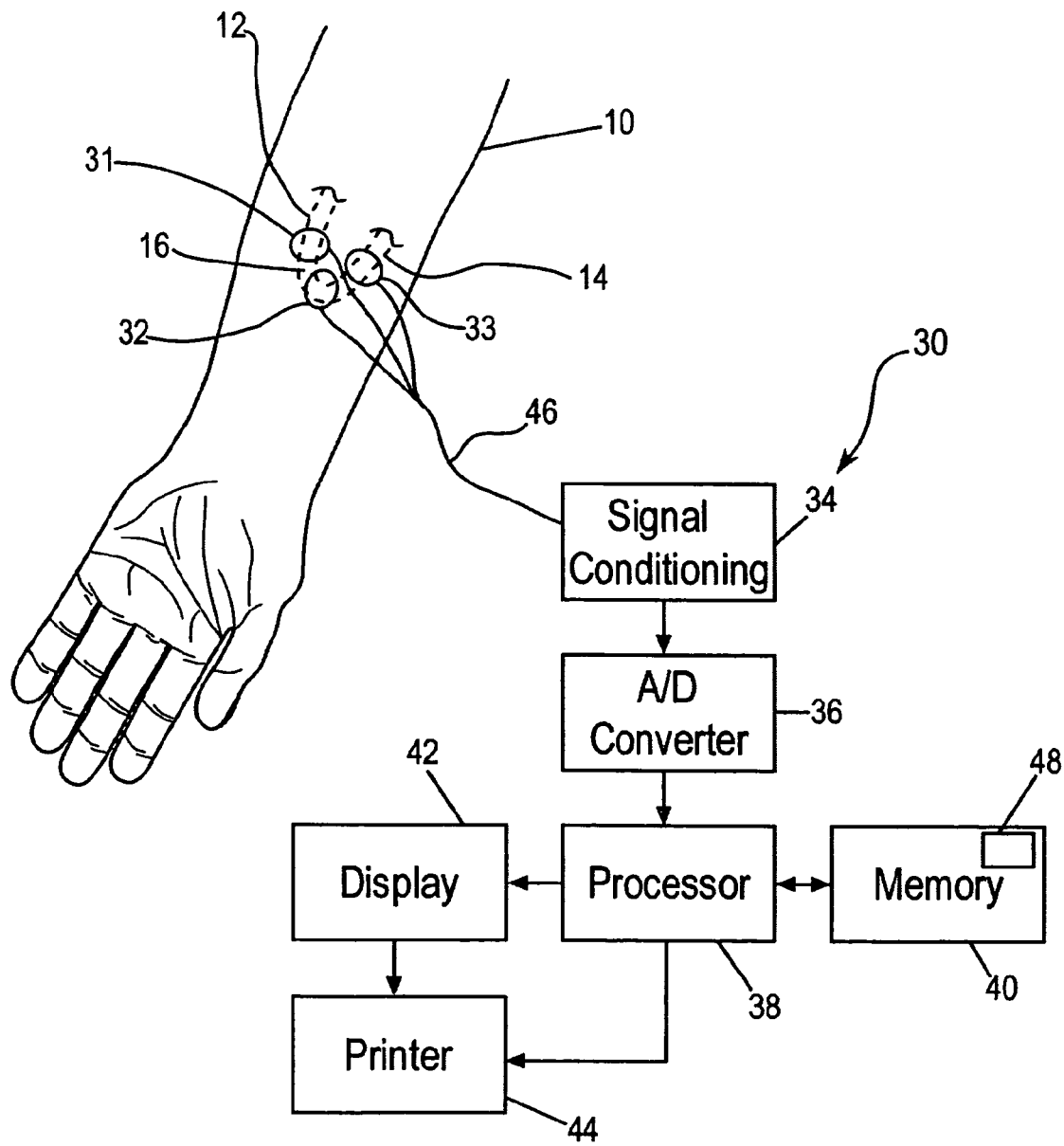
FIG. 2 is an exemplary schematic block diagram of an apparatus that may be used to assess the conditions within the shunt shown in FIG. 1.

FIG. 2 is an exemplary schematic block diagram of a system 30 that may be used to assess the conditions within the shunt 16 shown in FIG. 1. As shown in FIG. 2, the system 30 includes sensors 31-33, a signal conditioning block 34, an analog-to-digital (A/D) converter 36, a processor 38, a memory 40, a display 42 and a printer 44.

The sensors 31-33 may be contact or non-contact transducers that detect vibrations or sounds at or near the skin surface and convert these vibrations or sounds into electrical signals. By way of example only, the sensors 31-33 may be electronic stethoscopes, accelerometers, contact microphones, non-contact vibration sensors such as capacitive or optical sensors, or any other suitable type(s) of sensors. In some applications, an electret condenser air-coupled electronic stethoscope design may be selected for its sensitivity over a wide bandwidth, low cost, durability and ease of use. In any event, the sensors 31-33 are preferably, but not necessarily, selected to have an impedance that matches the impedance of the skin surface to provide optimal coupling to the skin surface. Still further, due to background noise and the relatively low amplitude of the vibrations or sounds that are generated at or near the skin surface by vascular blood flow, the sensors 31-33 are also preferably, but not necessarily, selected to provide a high signal-to-noise ratio, high sensitivity and suitable ambient noise shrouding capability. While three sensors are shown in FIG. 2, additional or fewer sensors may be used to detect vascular vibrations or sounds at multiple locations on the forearm 10, or any other locations on the patient's body that are of interest. For example, a single sensor may be strategically located on the patient's body and/or may be moved sequentially to different key locations on the patient's body to detect vascular vibrations or sounds.

The sensors 31-33 send low level (i.e., low power) electrical signals via wires 46, or any other suitable media such as wireless radio frequency, infrared, etc., to the signal conditioning block 34. The signal conditioning block 34 may include amplifiers, filters, transient protection and other circuitry that amplifies the signals sent by the sensors 31-33, attenuates noise signals, and reduces the effects of aliasing. In particular, the signal conditioning block 34 may include a low-pass filter having a cutoff frequency of about 2000 Hertz (Hz). Alternatively or additionally, a high-pass filter may be incorporated within the signal conditioning block 34. This high-pass filter may, for example, have a cut-off frequency of about 75 Hz so that undesirable noise, such as muscle noise or other low frequency noise, is substantially attenuated or eliminated before the signals sent by the sensors 31-33 are processed further.

The A/D converter 36 receives the signal conditioned analog output signals from the signal conditioning block 34 and converts the received analog signal values into digital vibration information, which can be processed by the processor 38 as described in greater detail below. The processor 38 may be integral to a personal computer, may be integral to a microcontroller integrated circuit chip, may be implemented using a custom integrated circuit chip, or may be implemented using any other electronic device suitable for implementing the apparatus and/or carrying out the methods described herein.

The memory 40 is communicatively coupled to the processor 38 and may include machine readable (and machine executable) instructions or software 48 that, when executed by the processor 38, cause the processor 38 to carry out the methods described herein. It should be recognized that the processor 38 and the memory 40 may be integral to a personal computer or, alternatively, may be implemented using one or more custom, semi-custom or commonly available integrated circuits. Further, it should be recognized that the software 48 may include one or more software routines that are implemented using any of a variety of programming techniques and languages without departing from the scope and the spirit of the invention.

The display 42 may be any conventional video monitor or any other suitable display that communicates with the processor 38 and which can display graphic and/or textual information relating to the vascular sounds and vibrations detected by one or more of the sensors 31-33. Thus, the information generated on the display 42 may enable medical personnel to make a diagnosis of the vascular conditions within a patient's body. For example, the display 42 may graphically represent the temporal and/or spectral characteristics of the vascular sounds or vibrations detected at a particular location of the patient's body, which may be associated with, for example, a critical vascular structure such as an artery that supplies blood to a critical organ or a shunt, which is typically susceptible to stenosis and a variety of other pathologies. The displayed temporal and/or spectral characteristics may then be used to determine if an abnormal vascular condition exists by, for example, comparing the acquired temporal and/or spectral characteristics to reference temporal and/or spectral characteristics associated with a normal or acceptable condition and/or comparing the acquired temporal and/or spectral characteristics to a baseline condition. In addition, the acquired temporal and/or spectral characteristics may further be used to determine the precise location, type and severity of any abnormal condition present.

The printer 44 may be used to generate hard copies of textual and/or graphical information, including the information which is displayed on the display 42. For example, numerical and graphical temporal and/or spectral information may be printed to facilitate off-line analysis of test results by medical personnel and/or to facilitate the generation of permanent test results documentation for records, reports, etc.

Before discussing the operation of the system 30 shown in FIG. 2 in more detail, a general discussion of the acoustic characteristics of vascular blood flow is provided below. In general, the partial occlusion of blood flow causes the turbulence characteristics of the blood flow to change. These turbulence characteristics, in turn, are manifested as vibrations or sounds that can be detected at the skin surface. As will be described in greater detail below, an occluded or stenotic condition may cause the spectral energy of these turbulence induced vibrations or sounds to shift toward higher frequencies slightly downstream of the occlusion or stenosis. Additionally, as will also be discussed in greater detail below, relative acoustic spectral changes over an affected anastomotic region may be indicative of an occlusion.

As is well known, fluid flowing through a conduit produces turbulence which, in turn, may produce sounds in the audible frequency range. The characteristics of these audible turbulence sounds are determined by many variables, including conduit course and geometry, flow volume and velocity, conduit dimensions, conduit wall elasticity, etc.

More specifically, as fluid approaches a narrowed cross-section within the conduit, the fluid velocity increases and the fluid flow characteristics in the narrowed region depend on the conduit geometry and flow properties associated with the Reynolds number. For example, when there is only a slight decrease in conduit diameter and/or when the Reynolds number is low (e.g., due to a low fluid velocity), the fluid attaches to the conduit wall and typically only small vibrations are imparted to the conduit wall.

On the other hand, where there is a large decrease in conduit diameter and/or a high Reynolds number (e.g., due to high flow velocities), the fluid typically detaches from the conduit wall. Slightly downstream of the minimum crosssectional area (which is the same as the minimum diameter point if the cross-section is substantially circular), at a point called the vena contracta, the fluid attains a maximum velocity and minimum pressure. Then, as the flow area increases, the flow reattaches to the conduit wall and the average flow velocity decreases. In the case of vascular blood flow, the detached flow region may extend significantly downstream. For example, for an 85% stenosis and a Reynolds number of 200-2000, the blood flow may reattach to the vessel wall two to four vessel diameters downstream from the region of minimum cross-section (i.e., the stenosis).

When the Reynolds number is more than 325, the shear layer that forms in the detached flow region becomes highly unstable and causes strong velocity fluctuations or turbulence. This turbulence in the shear layer downstream of the constriction (e.g., a stenosis) causes relatively large conduit wall pressure oscillations, which may be coupled to neighboring structures. The amplitude of these wall pressure variations is a measure of turbulence intensity and is known to increase as the Reynolds number increases.

Figure 3:
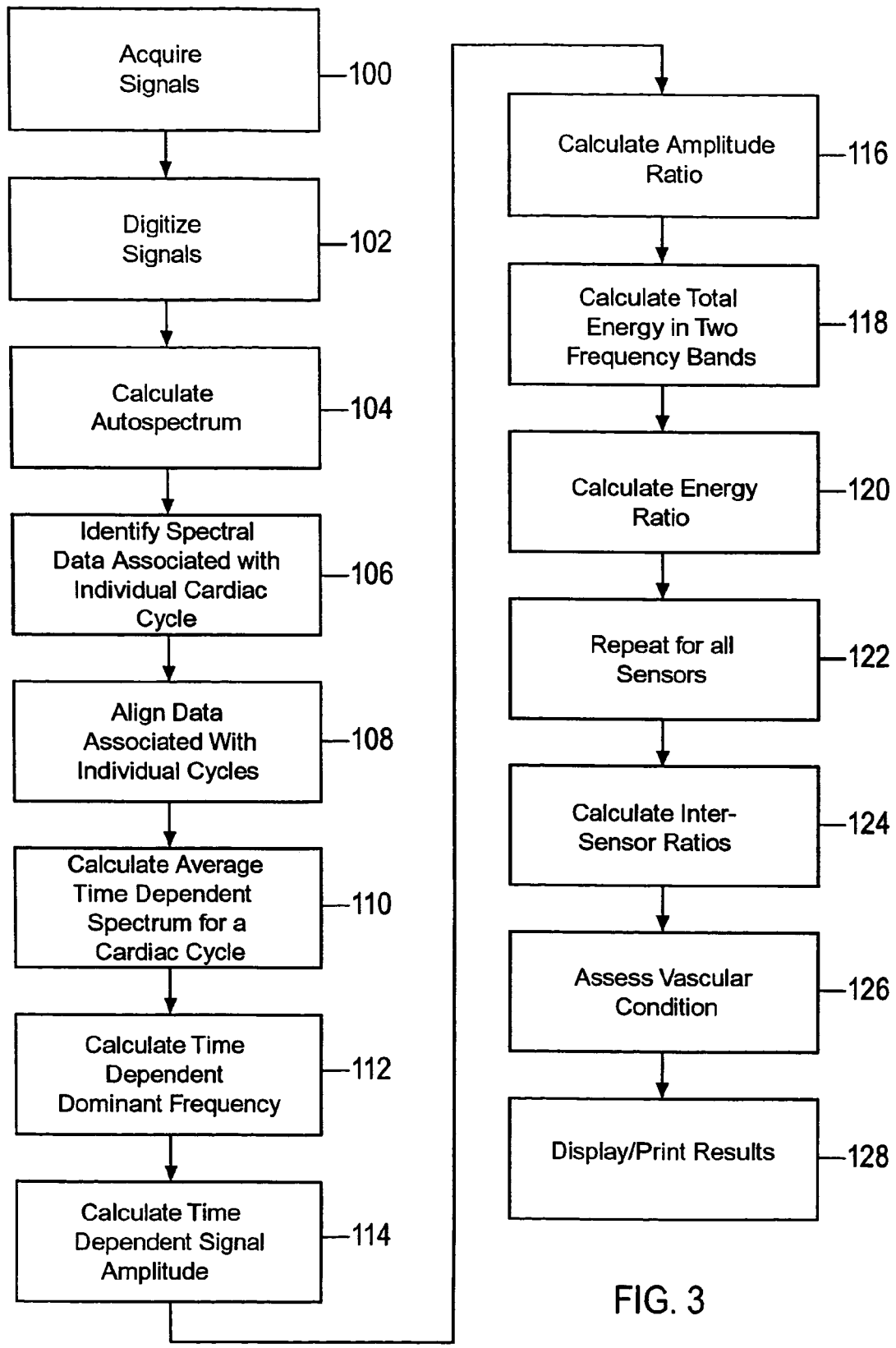
FIG. 3 is an exemplary flow diagram that represents one method by which the apparatus shown in FIG. 2 may process acoustic signals to assess the conditions within the shunt shown in FIG. 1.

FIG. 3 is an exemplary flow diagram that represents one method by which the apparatus shown in FIG. 2 may process acoustic signals to assess the conditions within the shunt 16 shown in FIG. 1. Block 100 acquires analog electrical signals from one or more of the sensors 31-33 (FIG. 2). Block 100 may use the signal conditioning block 34 (FIG. 2) to filter noise, amplify the signals, etc. as discussed above before the signals are processed by block 102. Further, block 100 may acquire signals from one or more of the sensors 31-33 for a period of time sufficient to capture vascular sounds or vibrations that are generated during one or more cardiac cycles. For example, block 100 may acquire signals from one or more of the sensors 31-33 for a period of time equal to the time required to complete ten cardiac cycles. Of course, block 100 may acquire sounds or vibrations for a period of time that corresponds to more or fewer cardiac cycles.

The sensors 31-33 may be arranged in any desired manner to facilitate the acquisition of vibrations and sounds associated with vascular blood flow turbulence and to facilitate the detection of vascular pathologies such as, for example, stenoses, occlusions, etc. In particular, in the case of the shunt 16, one of the sensors 31-33 (e.g., the sensor 32) may be located directly over the central portion of the shunt 16 (the location of which is typically precisely known because it is surgically placed) and the sensors 31 and 33 may be located upstream and downstream, respectively. Alternatively, the sensors 31 and 32 may be eliminated and the sensor 33 may be used to acquire signals representative of the acoustic characteristics of the shunt 16 in a region adjacent to a suspected stenosis or occlusion. Additionally, the sensor 33 may be moved to locations other than that specifically depicted in FIG. 2 to suit the needs of a particular application.

Block 102 converts the analog signals acquired by block 100 into digital data or information using, for example, the A/D converter 36 shown in FIG. 2. Typically, but not necessarily, the analog data is digitized at a sampling rate of 8192 Hz. However, other sampling rates may be used to achieve any desired frequency resolution.

Block 104 calculates the time dependent autospectrum (i.e., the time dependent spectral characteristics) of the digitized data provided by block 102. As is well known, the autospectrum may be graphically represented using a three-dimensional plot in which the x and y axes correspond to time and frequency and the z axis corresponds to spectral power. See, for example, FIGS. 7 and 8. Typically, but not necessarily, the autospectrum is calculated by performing fast Fourier transforms (FFTs) on overlapping segments of the digitized data. For example, if a 1024 point FFT is desired, the data segments may be defined as 125 milliseconds (ms) in duration with a 50% overlap. However, different data segment lengths and overlap percentages may be used instead to achieve any desired time and frequency resolution. Additionally, other data analysis techniques or algorithms such as autoregressive modeling or wavelets may be used instead of or in addition to FFTs to transform the digitized analog data into frequency domain or spectral information.

Block 106 identifies the spectral data associated with each of the individual cardiac cycles using any suitable data analysis technique. For example, autocorrelation of the acquired signals, autocorrelation of the acquired signal envelope and/or autocorrelation of the time dependent spectrum may be used to identify those portions of the spectral data produced by block 104 that are associated with each of the cardiac cycles for which block 100 has acquired signals. Block 108 then temporally aligns the portions or groups of spectral data associated with the individual cardiac cycles. This temporal alignment may be performed, for example, by aligning spectral peaks or by searching for the best time shift by calculating the autocorrelation of the time dependent spectrum at different frequencies. Of course, where block 100 only acquires data for a single cardiac cycle, blocks 106 and 108 do not necessarily have to be performed.

Block 110 uses the temporally aligned groups of spectral data generated by block 108 to calculate an average time dependent spectrum for the cardiac cycles. Block 110 may, for example, average (i.e., ensemble average) the temporally aligned time dependent spectra corresponding to each of the cardiac cycles. However, any other averaging technique that produces the time dependent spectral characteristics for a typical cardiac cycle may be used instead. Block 112 then uses the average time dependent spectrum for a typical cardiac cycle calculated by block 110 to determine the time dependent dominant frequency, which is the frequency having the largest spectral energy at each instant of time. See, for example, FIGS. 9 and 11.

Block 114 uses the time dependent spectrum for an average cardiac cycle to calculate the time dependent signal amplitude of the average cardiac cycle by summing the energies of all frequency data points at each instant of time. Alternatively, block 114 may calculate the time dependent signal amplitude of the average cardiac cycle by determining the amplitude of the Hilbert transform of the blood flow acoustic signals. Block 116 then determines the amplitudes associated with the time dependent signal amplitude of the average cardiac cycle, which is generated by block 114, at two different parts of the average cardiac cycle. For example, the points within the average cardiac cycle that correspond to the minimum and maximum amplitudes may be selected. After block 116 has determined the amplitudes, block 116 calculates the ratio of the amplitudes.

Block 118 uses the average time dependent spectrum calculated in block 110 to calculate the total energy in two or more predetermined frequency bands. By way of example only, the frequency bands may be 50-175 Hz and 200-400 Hz. However, other frequency bands may be used instead. Further, the total energy within the predetermined frequency bands may be calculated over all parts of the cardiac cycle (i.e., using the total spectral power for a single cardiac cycle) by summing the spectral power for each frequency of the time dependent spectrum over all time intervals.

Alternatively, the total energy within the predetermined frequency bands may be calculated at different parts of the cardiac cycle. In other words, the total energy within one of the predetermined frequency bands may be calculated at one time within the cardiac cycle and the total energy within another one of the predetermined frequency bands may be calculated at a different time within the cardiac cycle (using the time dependent spectrum calculated by block 110). Block 120 then uses the total energy values calculated by block 118 to calculate energy ratios. For example, the total energy associated with a high frequency band (e.g., 200 Hz to 400 Hz) may be divided by the total energy associated with a low frequency band (e.g., 50 Hz to 175 Hz).

Block 122 may then repeat the activities of blocks 100 through 120 for all of the sensors (e.g., the sensors 31-33) that are currently being used to detect vascular sounds and vibrations and block 124 may use data associated with two or more of the sensors 31-33 to calculate inter-sensor amplitude ratios and/or inter-sensor energy ratios. Block 126 may then use the time dependent dominant frequency information, the amplitude ratios and/or the energy ratios for one or more of the sensors 31-33 to assess the patient's vascular condition. Alternatively or additionally, the inter-sensor ratios may be used to assess the patient's vascular condition.

While the system 30 shown in FIG. 2 is described by way of example as being adapted to process the acoustic signals acquired by the sensors 31-33 using digital signal processing techniques, analog signal processing techniques may be used instead to process vibration or sound information to achieve the same or similar results. For example, an analog filter bank may be used to separate the energy associated with different energy bands and one or more comparators may be used to make relative comparisons between the energy values of the different bands.

As will be discussed in greater detail below in connection with FIGS. 5-12, the acoustic characteristics associated with different vascular conditions may vary significantly from one condition to another. Thus, the acoustic characteristics associated with each known vascular condition may be determined in advance and parameter values such as, for example, values for the time dependent dominant frequency, the amplitude ratio and/or the energy ratios may be developed for each vascular pathology. In this manner, block 126 may assess a patient's vascular condition by comparing the calculated dominant frequency, amplitude ratio and/or energy ratio values to one or more sets of predetermined parameter values, each of which contains values that are indicative of a particular vascular condition or pathology. Further, block 126 may use neural network techniques, which are well known, to produce a resultant value based on one or more of the calculated parameters.

In addition, for some vascular conditions, patient to patient variability may be substantial, which significantly reduces or eliminates the discriminatory power that a predetermined set of parameter values affords the assessment of the vascular condition performed by block 126. For assessment of vascular conditions in which variability between patients is relatively high, a set of baseline parameter values may be developed for each patient and relative comparisons of calculated parameter values to these baseline values may be made to more precisely assess the vascular conditions within that particular patient. Vascular assessment using such baseline values is discussed in greater detail below in connection with FIG. 13.

Figure 4:
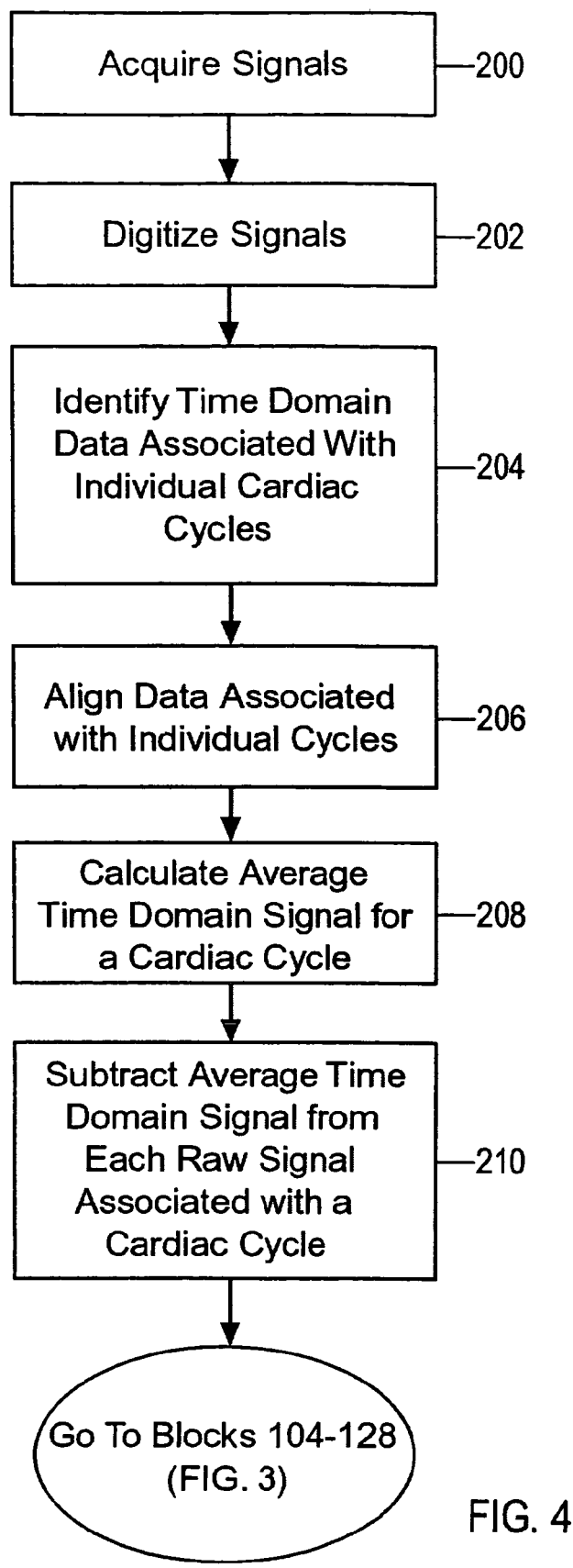
FIG. 4 is an exemplary flow diagram that represents another method by which the apparatus shown in FIG. 2 may process acoustic signals to assess the conditions within the shunt shown in FIG. 1.

FIG. 4 is an exemplary flow diagram that illustrates another method by which the apparatus shown in FIG. 2 may process acoustic signals to assess the conditions within the shunt 16 shown in FIG. 1. Blocks 200 and 202 acquire and digitize signals in manners identical to that of blocks 100 and 102, the operations of which are described above in connection with FIG. 3. Block 204 then identifies the groups of time domain data that are associated with each of the individual cardiac cycles and block 206 temporally aligns the groups of time domain data identified by block 204. Block 206 may use any suitable technique such as, for example, autocorrelation of the time domain signal or signal amplitude calculated as in block 114 above, to perform the temporal alignment.

Block 208 then averages the temporally aligned groups of time domain data generated by block 206 to calculate the time domain signal for an average cardiac cycle. Block 210 then subtracts this average time domain signal from each of the groups of time domain information (i.e., the individual cardiac cycles) identified by block 204. In this manner, block 210 produces difference signals which are representative of the non-repeatable or non-cyclical portions of each cardiac cycle acquired by block 200. The characteristics of these difference signals (i.e., the non-repeatable acoustic information) may then be processed by blocks 104-128 shown in FIG. 3, thereby enabling an assessment of a patient's vascular condition based on non-repeatable signal characteristics.

Figure 6:
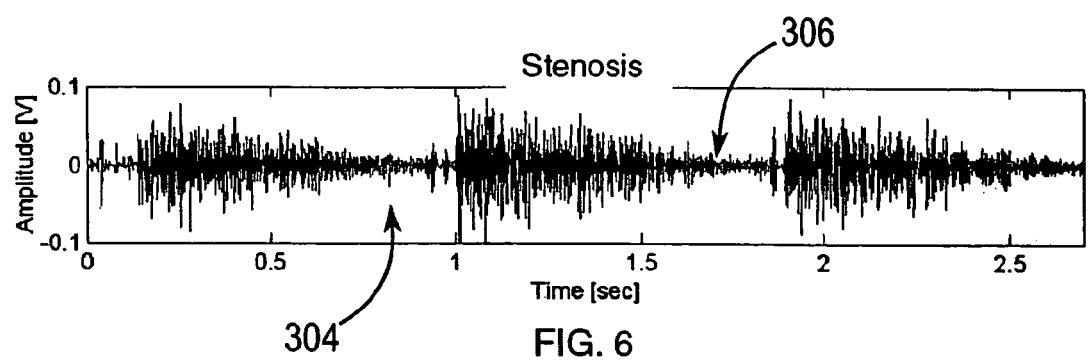
FIG. 6 is an exemplary graphical representation of an electrical signal obtained by measuring the sounds generated within a vascular shunt having a stenosis.
Figure 5:
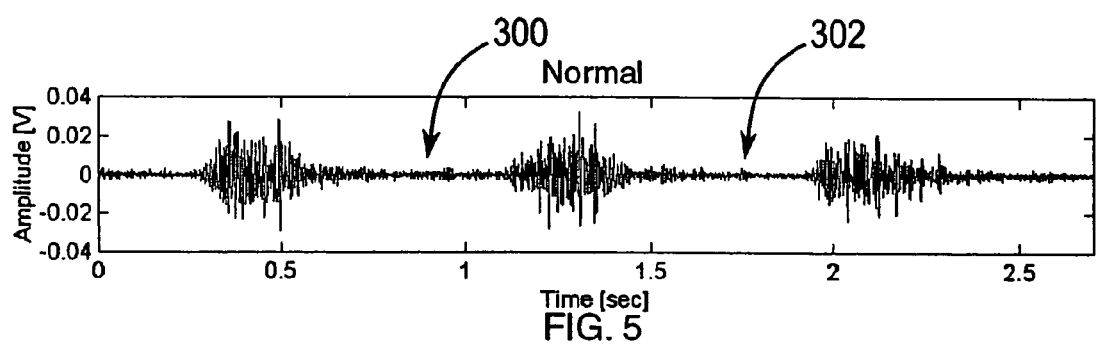
FIG. 5 is an exemplary graphical representation of an electrical signal obtained by measuring the sounds generated within a vascular shunt having normal patency.

FIG. 5 is an exemplary graphical representation of an electrical signal obtained by measuring the sounds generated at the skin surface adjacent to a vascular shunt having normal or acceptable patency. FIG. 6, on the other hand, is an exemplary graphical representation of an electrical signal obtained by measuring the sounds generated at the skin surface adjacent to a vascular shunt having a stenosis. The electrical signals shown in FIGS. 5 and 6 are more than 2.5 seconds in duration and, in this case, include vascular sounds generated during three cardiac cycles. The electrical signals may be acquired, for example, using the methods shown in FIGS. 3 and 4 in conjunction with the apparatus 30 shown in FIG. 2. More specifically, blocks 100 and/or 200 may acquire the signals using one or more of the sensors 31-33 and the signal conditioning block 34. Of course, the electrical signals may be acquired over a longer or a shorter time period and, thus, may include more or fewer cardiac cycles, if desired.

A comparison of the signals shown in FIGS. 5 and 6 reveals that the peak-to-peak amplitudes of the signal generated when a stenosis exists within the vascular structure being monitored is, generally speaking, much greater than the peak-to-peak amplitudes of the signal generated under normal conditions (i.e., when the stenosis is relieved, eliminated or absent). In particular, FIG. 6 shows, by way of example only, a peak-to-peak amplitude of about 200 millivolts (mV), whereas FIG. 5 shows a peak-to-peak amplitude of less than about 75 mV. Further, it can be seen from FIGS. 5 and 6 that the noise level present in the regions between cardiac cycles, such as the regions 300 and 302 shown in FIG. 5, is relatively low compared to the corresponding regions 304 and 306 shown in FIG. 6.

Figure 8:
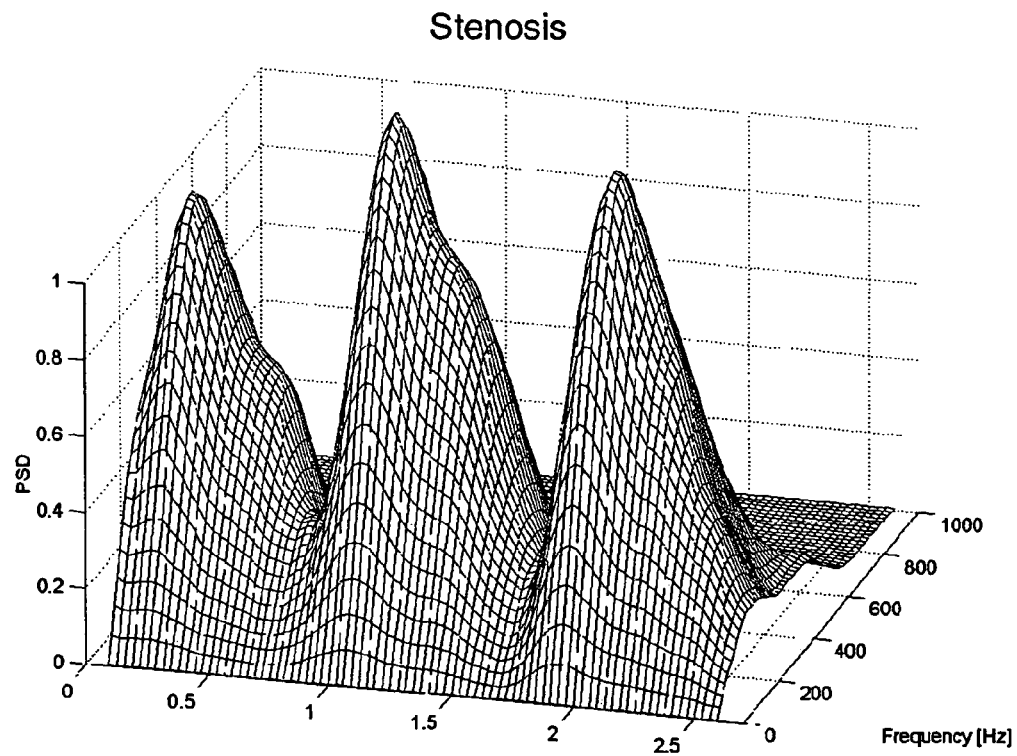
FIG. 8 is an exemplary graphical representation of the time dependent spectral characteristics of the electrical signal shown in FIG. 6.
Figure 7:
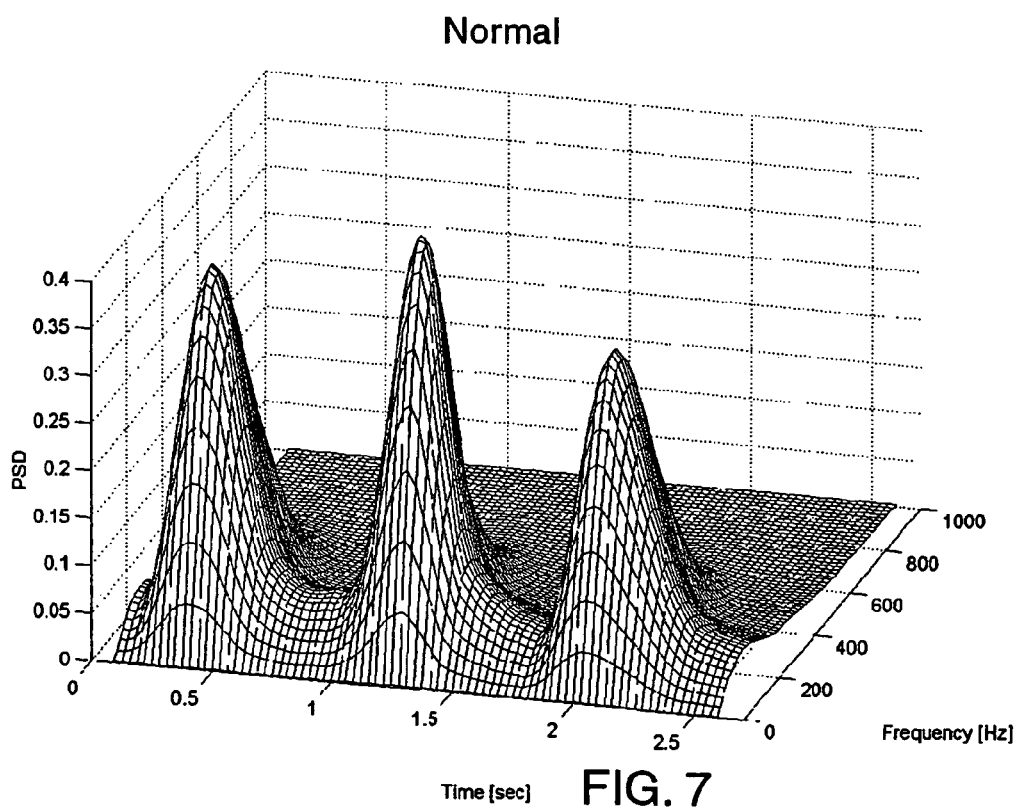
FIG. 7 is an exemplary graphical representation of the time dependent spectral characteristics of the electrical signal shown in FIG. 5.

FIG. 7 is an exemplary graphical representation of the time dependent spectral characteristics of the electrical signal shown in FIG. 5, and FIG. 8 is an exemplary graphical representation of the time dependent spectral characteristics of the electrical signal shown in FIG. 6. Thus, the spectral characteristics shown in FIG. 7 are associated with a normal vascular condition, whereas the spectral characteristics shown in FIG. 8 are associated with a stenotic vascular condition. As can be clearly seen from FIGS. 7 and 8, the spectral power associated with a wide range of frequencies increases substantially when a stenotic vascular condition is present. As noted above, this increased spectral power may be directly due to the increased turbulence that a stenosis produces slightly downstream of or adjacent to the stenotic region.

Figure 12:
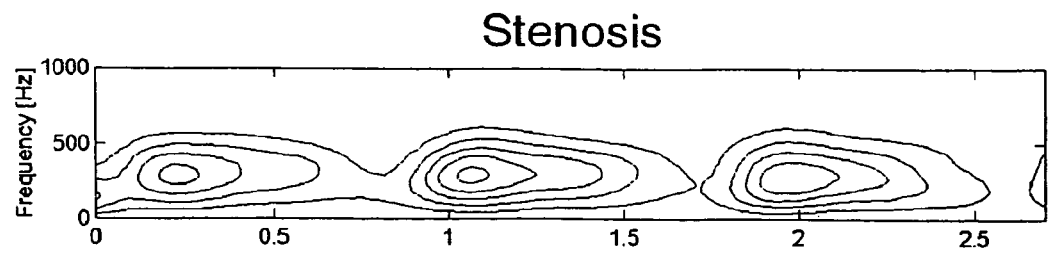
FIG. 12 is an exemplary contour plot of the time dependent spectral characteristics shown in FIG. 8.
Figure 11:
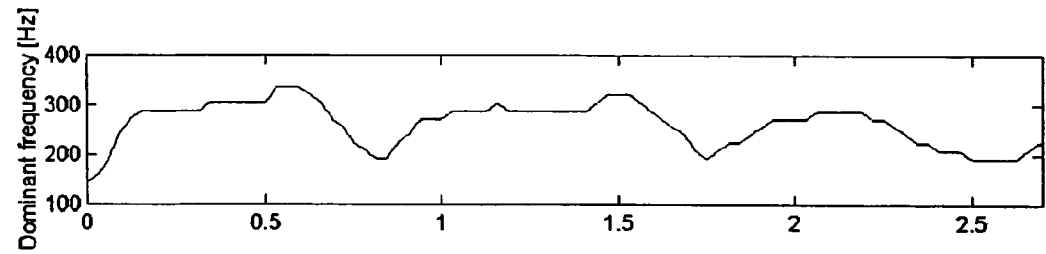
FIG. 11 is an exemplary graphical representation of the time dependent dominant frequency of the electrical signal shown in FIG. 6.
Figure 10:
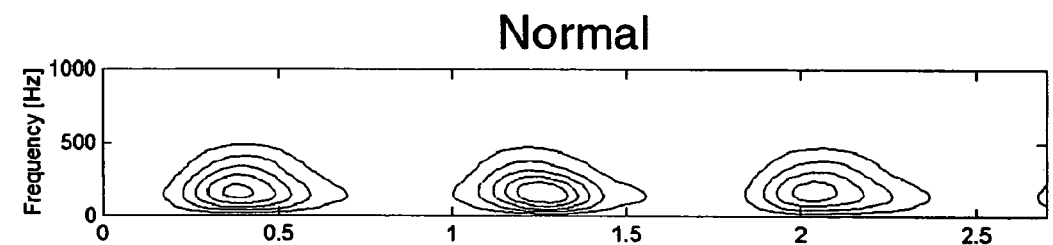
FIG. 10 is an exemplary contour plot of the time dependent spectral characteristics shown in FIG. 7.
Figure 9:
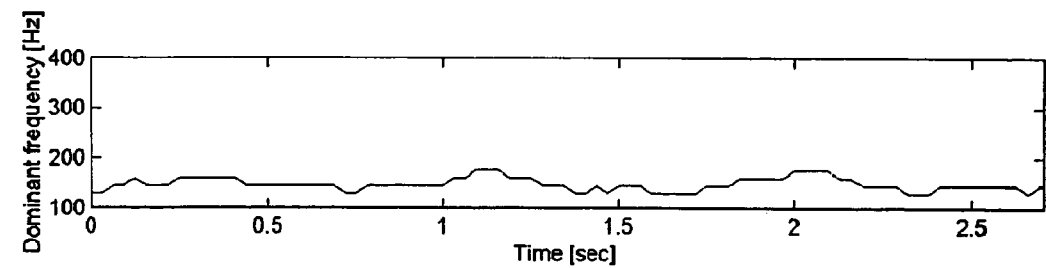
FIG. 9 is an exemplary graphical representation of the time dependent dominant frequency of the electrical signal shown in FIG. 5.

FIG. 9 is an exemplary graphical representation of the time dependent dominant frequency of the electrical signal shown in FIG. 5, and FIG. 10 is an exemplary contour plot of the time dependent spectral characteristics shown in FIG. 7. Similarly, FIG. 11 is an exemplary graphical representation of the time dependent dominant frequency of the electrical signal shown in FIG. 6, and FIG. 12 is an exemplary contour plot of the spectral characteristics shown in FIG. 8. As clearly shown by FIGS. 9-12, the temporal and/or spectral characteristics associated with a normal vascular condition are significantly different from the temporal and/or spectral characteristics associated with a stenotic vascular condition.

In any event, the significant differences in the temporal and/or spectral characteristics, which are depicted by way of example in FIGS. 5-12, may be used in conjunction with the methods described herein to detect the location and/or type and degree of a vascular abnormality.

In one test on a 65 year old female suspected to have AV graft stenosis, the methods and apparatus described herein were used to measure acoustic characteristics both before and after angioplasty of an affected region associated with the graft. A 90% stenotic region was found and was verified to improve by 50% post angioplasty.

After digitization at 8192 Hz, the power spectral density was calculated using an FFT with Hanning windowing to provide a resolution of about 16 Hz. The mean spectral densities were then calculated for pre and post angioplasty states by averaging the data from each 125 ms acquisition segment. The dominant frequency was then found by determining the frequency having the highest power level within the mean spectral density function. In a pre-angioplasty state the dominant frequency was found to be 270+/−74 Hz and in the post angioplasty state the dominant frequency was found to be 125+/−31 Hz. A Z-test was used to determine the statistical significance of the results. In this case, the Z-test resulted in a p value of 0.03, which indicates a high probability that a shift of spectral energy had in fact occurred.

Figure 13:
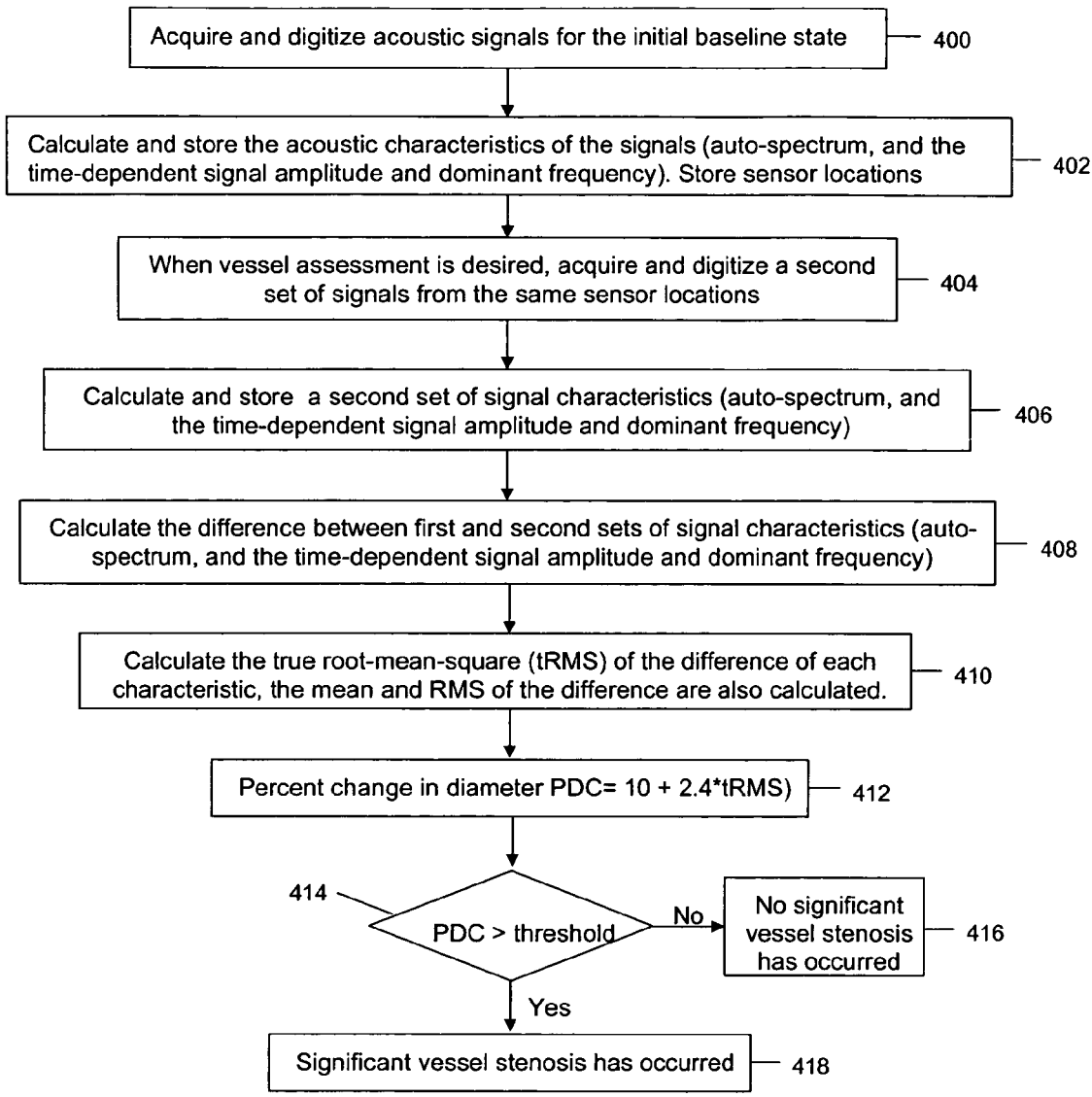
FIG. 13 is an exemplary flow diagram that represents one method by which the apparatus shown in FIG. 2 may process signals to assess vascular conditions using baseline acoustic characteristics.

FIG. 13 is an exemplary flow diagram that illustrates one manner in which the apparatus shown in FIG. 2 may be configured to assess vascular conditions using baseline measurements. More specifically, with the example method of FIG. 13, the condition of vascular structures (e.g., blood vessels) may be monitored by comparing the characteristics of current vascular sounds, which are associated with a current state of vascular condition, to the acoustic characteristics associated with a baseline state of the vascular condition. To establish baseline acoustic characteristics, block 400 acquires and digitizes a first set of acoustic signals from a plurality of skin surface locations using acoustic sensors in manners similar or identical to those described above in connection with blocks 100 and 102 (FIG. 3). The acquisition time employed at block 400 may be, for example, between ten and thirty seconds, or any other suitable time period. Preferably, but not necessarily, the condition (e.g., the percentage stenosis) of the vascular structure being monitored to establish the baseline characteristics is known at the time the baseline characteristics are established. For example, at the time the baseline characteristics are established, the vascular structure being monitored may be known to be in a healthy condition, an unhealthy condition, to have a certain degree (e.g., percentage) of stenosis, etc.

Block 402 receives the digitized acoustic signal information from block 400 and generates or calculates the baseline acoustic characteristics of the vascular structure being monitored. In particular, block 402 may generate and store (e.g., in a memory) spectral information (e.g., an average time-dependent spectrum), time-dependent amplitude (also referred to as an envelope) information and dominant frequency information for use as baseline information in subsequent analyses. The locations (e.g., relative to anatomic landmarks or predetermined locations on a patient's body) of the sensors or transducers (e.g., the sensors 31-33) used to acquire the acoustic signal information at block 400 may also be determined and stored at block 402. In some example implementations, a template indicating the sensor locations and the anatomic locations or landmarks is generated and stored in a patient chart or record for subsequent use. Further, each sensor used may have its own set of acoustic characteristics information generated and stored. In addition, the acoustic spectra may be calculated for parts of a cardiac or respiratory cycle to increase stenosis detection accuracy. In some applications, the acoustic spectra may be calculated for the louder parts of the cycle being monitored. Subtracting the spectra of the lower flow parts of the cycle is also possible.

After baseline acoustic characteristics have been established (block 402), sensors may be removed from the patient and the patient may be released. Some time later, the patient may return for a subsequent assessment of the vascular structure for which baseline acoustic characteristics were previously established. In the case where sensors are removed after establishing the baseline acoustic characteristics, the sensors may be re-attached or otherwise coupled to the patient's body in accordance with the template information (i.e., the sensor location information) stored during the acquisition of the baseline acoustic characteristics. However, in other examples, the patient may be not be released and, thus, the sensors may not be removed prior to such a subsequent assessment of the vascular structure.

In any case, as described in greater detail below, a subsequent assessment of a vascular structure (i.e., following establishment of the baseline acoustic characteristics of the vascular structure) may compare the current acoustic characteristics of the vascular structure being monitored to the earlier established baseline acoustic characteristics to determine if, for example, a significant change in the vascular structure (e.g., a significant stenosis of the vascular structure) has occurred. In particular, block 404 acquires and digitizes acoustic signals from the same sensors (located in the same positions) as those used to establish the baseline information at blocks 400 and 402. Block 406 receives the digitized acoustic signal information from block 404 and generates and stores acoustic characteristic information associated with the current condition of the vascular structure being monitored. In particular, block 406 generates and stores autospectrum information, time-dependent signal amplitude information and dominant frequency information for each of the sensors used to monitor the vascular structure.

The baseline spectral information generated at block 402 and the subsequent spectral information generated at block 406 may be calculated using an FFT analysis. In particular, the signals being analyzed may be split into overlapping segments, the spectrum for each segment may be calculated, and the average of all spectra may then be calculated. In one implementation, the segment length may be 250 ms with an overlap of 125 ms to provide a frequency resolution of 4 Hz. Additionally, the envelope information and the time dependent dominant frequency information may be calculated in manners that are similar or identical to those described above in connection with blocks 106 through 114. However, other methods of generating spectral information, envelope information and/or dominant frequency information may be used instead.

Block 408 calculates or determines the difference between the current acoustic characteristics of the vascular structure being monitored and the baseline acoustic characteristics established for that structure at block 402 on a sensor by sensor basis. For example, the current spectral information and the baseline spectral information associated with each sensor may be converted to decibels or any suitable logarithmic scale and the spectral difference (at each frequency bin) between the baseline spectrum and current spectrum may be calculated. In addition, block 408 also calculates the difference between the baseline and current time-dependent dominant frequency as well as the difference between baseline signal envelope and the current signal envelope, preferably after envelope normalization. Envelope normalization may be implemented by subtracting the minimum value of the envelope and dividing by the maximum envelope value so that the envelope values range between 0 and 1. However, other normalization ranges and methods ranges such as, for example, dividing by the envelope sum, could be used instead.

Block 410 then calculates the true root-mean-square (tRMS) of the spectral difference (without subtracting the mean spectral difference) for a given frequency range (e.g., 200-500 Hz). Block 410 also calculates the tRMS of the envelope and dominant frequency differences. The values calculated or generated at blocks 406, 408 and 410 are generated or calculated for each sensor.

In the example of FIG. 13, a change in a vascular structure (e.g., a percent change in a blood vessel diameter, PDC) may be estimated by block 412 using the equation PDC=10+2.4*tRMS for each sensor and each acoustic characteristic for each sensor. In this example, "PDC" may be equal to or otherwise related to a percentage diameter change in a vascular structure (e.g., a blood vessel). To determine if there are significant changes in a vascular structure (e.g., a change in vessel patency), block 414 compares the PDC values for each sensor to threshold values. If none of the PDC values exceeds a threshold value or threshold values, block 416 reports that no significant vascular (e.g., stenosis) change has occurred since baseline measurements were obtained. On the other hand, if at least one PDC value (one value for each sensor used) exceeds a corresponding threshold, then block 418 reports that a significant change (e.g., a significant change in vessel diameter) has occurred. Of course, other comparisons to threshold values are possible. For example, tRMS can be compared to a threshold value to assess or measure significance of a stenosis.

Alternatively or additionally, block 410 calculates the mean and the root mean square RMS (with the mean subtracted) of the spectrum, the envelope, and the dominant frequency differences. Mean and RMS values may be indicative of changes in a vascular condition. For example, mean spectral differences are indicative of acoustic amplitude changes, while the RMS of a difference is indicative of a redistribution of acoustic energy among different frequencies. The tRMS combines the mean and RMS in a single parameter that facilitates comparisons with thresholds. However, other combinations of the mean and RMS are possible. For example, adding the mean and RMS values and/or using the mean or RMS values separately result information indicative of vessel patency. Still further, mean and RMS calculations may also be used for the time dependent envelope and dominant frequency. For example the percent diameter change can be calculated using the equation PDC=8+0.6*(RMS of the differences of normalized envelopes).

The methods and apparatus described herein were used to measure acoustic characteristics both before and after angioplasty of the stenosed region of several patients. The stenosed regions of the patients were improved or relieved post angioplasty by varying degrees. The data management and analysis for each patient were preformed as described below.

After data acquisition from two sensors for 15 seconds in the pre and post angioplasty states, signals were digitized at 8192 Hz. An FFT was used to estimate spectral information for data segments, each of which was 250 ms in duration and overlapped by 125 ms with neighboring segments. The average spectrum was then calculated by averaging the spectral estimates associated with each of the data segments. In some cases, sensors were placed so that one sensor was as close as possible to the venus anastomoses and the other close to arterial anastomosis. The spectral differences between the pre- and post-angioplasty states were calculated for each sensor and the tRms, mean and RMS of the spectral difference were calculated. The tRMS, mean and RMS were also calculated for the difference between average cardiac cycle envelopes after normalization.

Figure 14:
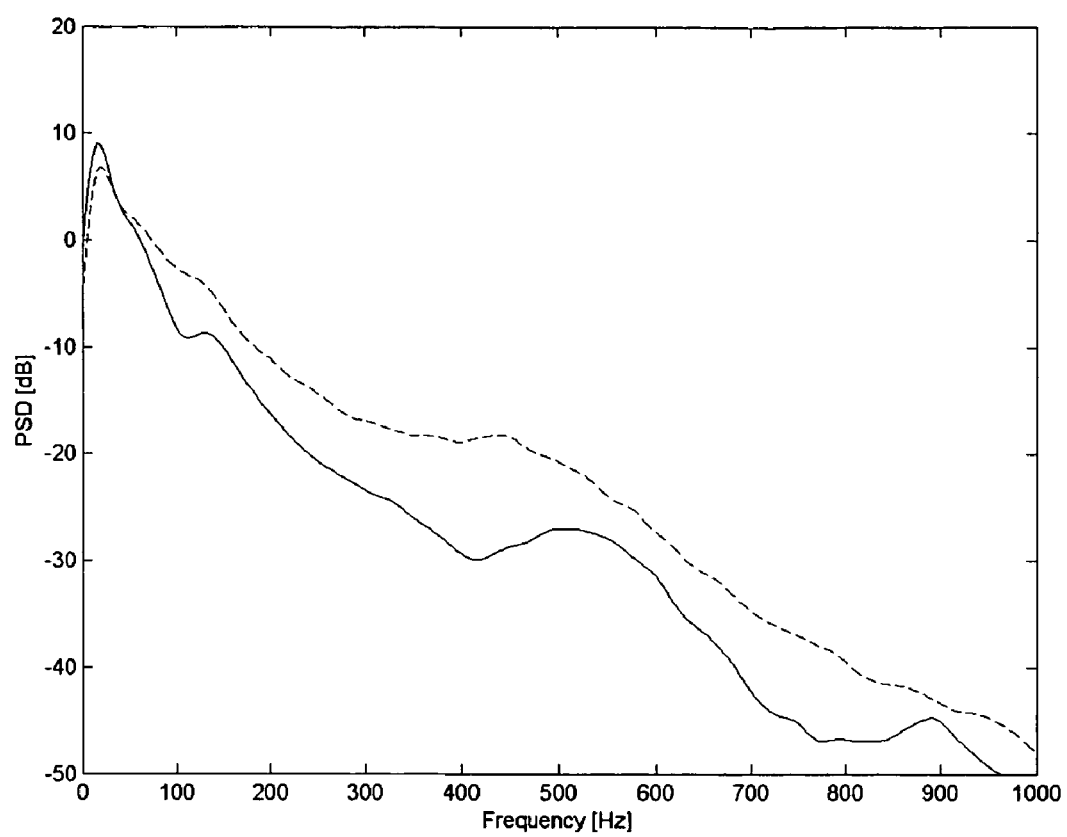
FIG. 14 is an exemplary graphical representation of the spectra of vascular sounds of a blood vessel in a stenosed condition and a relieved condition.
Figure 15:
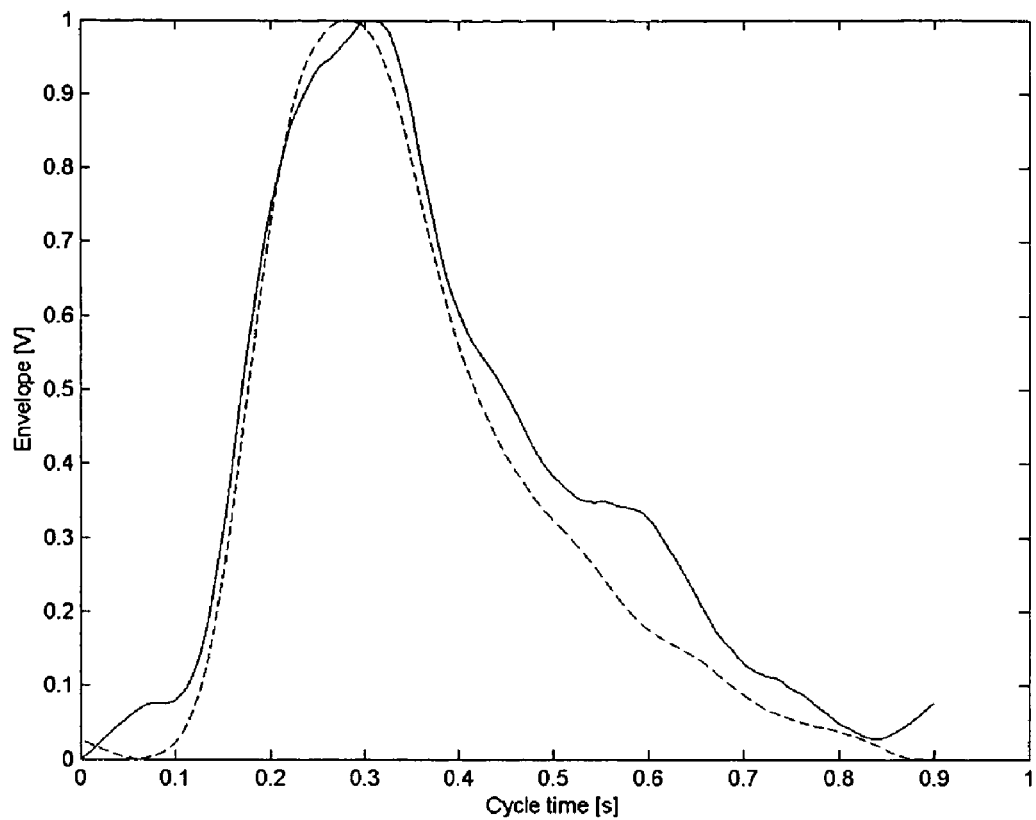
FIG. 15 is an exemplary graphical representation of the envelope of vascular sounds of an average cardiac cycle for a blood vessel in a stenosed condition and a relieved condition.

FIG. 14 is an exemplary graphical representation of the spectra for one patient. The pre- and post-angioplasty states (i.e., stenosed and non-stenosed states) are shown in solid and dashed lines, respectively. FIG. 15, shows the envelope of the average cardiac cycle for the patient of FIG. 14, where the pre- and post-angioplasty states are also shown with solid and dashed lines, respectively. Both the spectral data and the envelope data in FIGS. 14 and 15, respectively, exhibit differences due to a change in the vessel diameter in the stenosed region.

Figure 16:
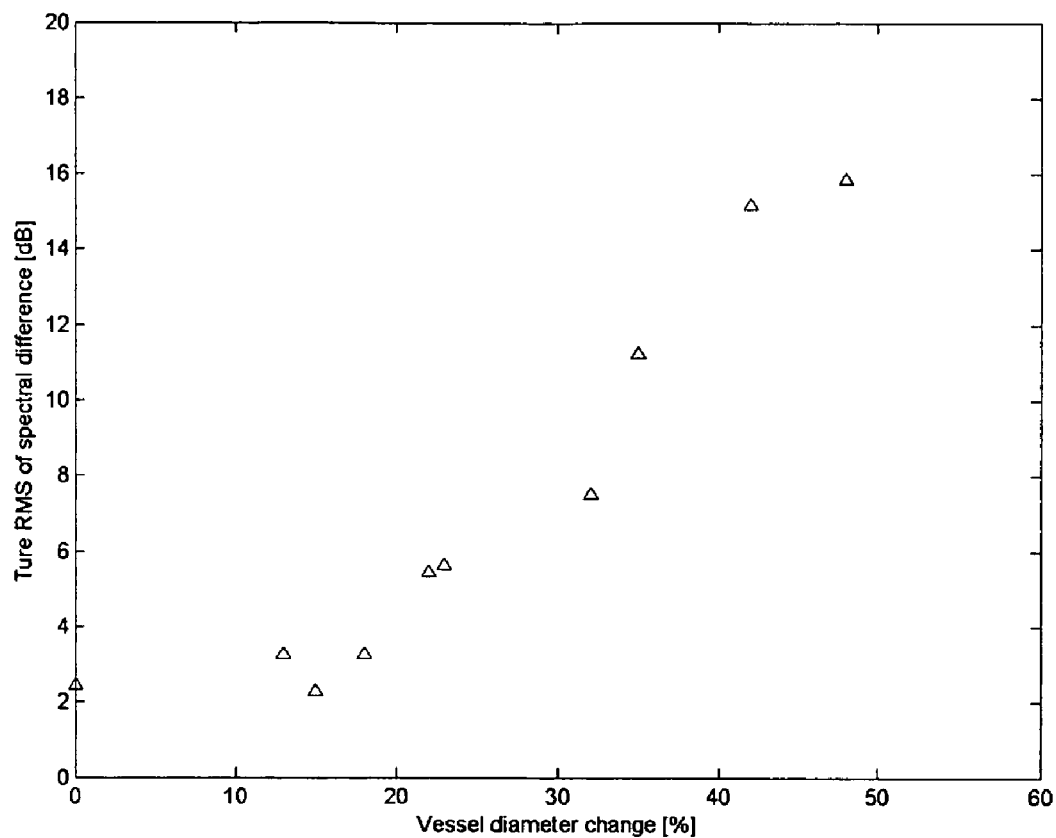
FIG. 16 is an exemplary graphical representation of the true root mean square (RMS) of the spectral difference between stenosed and relieved blood vessel conditions measured using multiple sensors for several subjects exhibiting different degrees of vessel diameter change.

FIG. 16 shows the tRMS of the spectral differences for all subjects as a function of the percentage change in their stenosis. As shown in FIG. 16, the largest of the tRMS values from the two sensor locations is plotted against the percent change in diameter. The latter was calculated as the difference in the diameter of the stenosed region divided by the native vessel diameter. However, other measures are possible by dividing by the maximum diameter of the stenosed region. FIG. 16 shows that the tRMS is indicative of the percent diameter change, where the relation may be represented using the equation PDC=10+2.4*tRMS.

It can also be seen from FIG. 16 that minor stenosis changes (e.g., less than 20%) can be separated from larger stenosis changes by a threshold of about 4 decibels (dB). As a result, the cut off between small and large stenosis values may be changed by changing the tRMS threshold value. For example an 8 dB threshold value would separate changes below 30% change from those above 30%. Similar data processing is possible using RMS, mean, or sum of mean and RMS of the differences between the different signal characteristics (such as spectra, envelope, or dominant frequency or time dependent spectrum at different frequencies).

Figure 17:
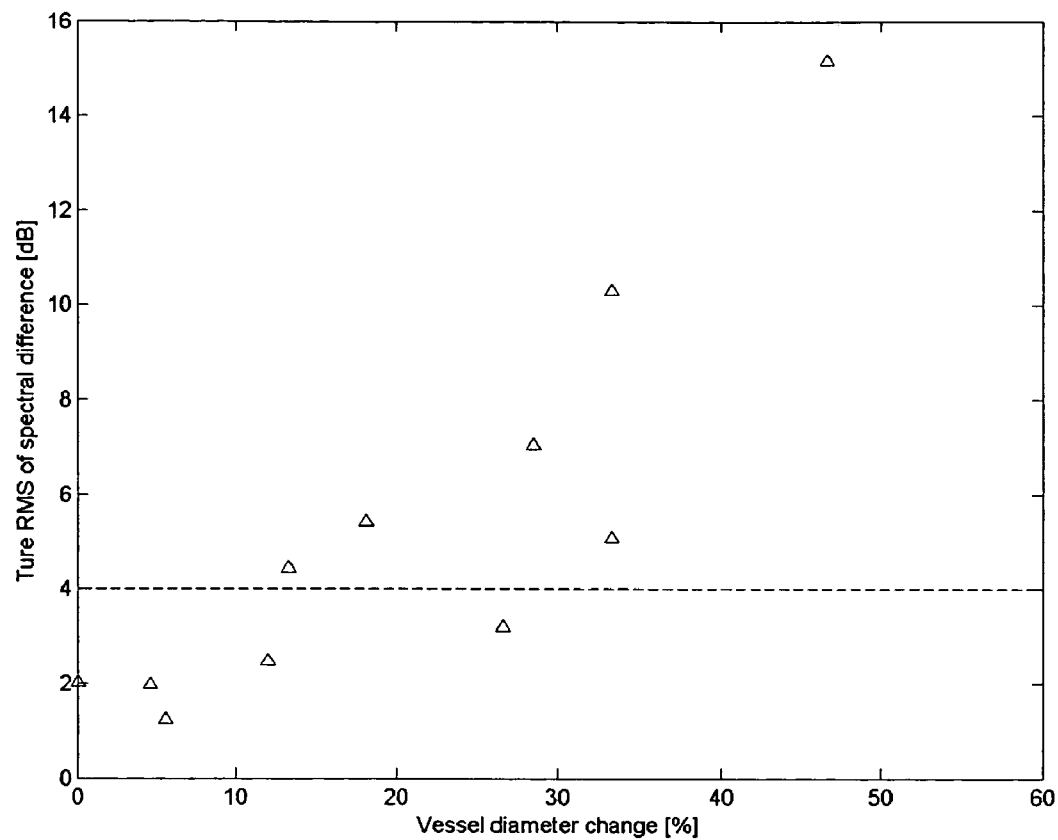
FIG. 17 is an exemplary graphical representation of the true RMS of the spectral difference between stenosed and relieved blood vessel conditions measured using a single sensor for several subjects exhibiting different degrees of vessel diameter change.

FIG. 17 shows the tRMS from a single sensor location versus the change in percent stenosis. The data is similar to that of FIG. 16 but evidences a greater degree of scatter. The greater degree of scatter shown in FIG. 17 may be due to the fact that the location of stenosis is not known beforehand and, as a result, the sensor location(s) may not have been optimal. However, by using multiple locations (e.g., two locations are used in the example of FIG. 1), the probability of optimally locating sensors increases, and better correlation can be found between the percent stenosis change and the acoustic characteristics. Because the data of FIG. 16 shows that two sensor locations may provide good correlation between the tRMS and the PDC value, it is clear that a plurality of sensor locations yields better assessment. Additionally, from the foregoing, two sensor locations appear to provide a good compromise between insufficient discrimination (e.g., when one sensor is used at a non-optimal location) and increased system cost and complexity (e.g., when a large number of sensors is used).

While the signal analyses described above focused on the 200-500 Hz band (and filtered other frequencies) other frequency bands could be used instead. The frequency band was selected to maximize the correlation between the tRMS of the spectral difference and the percent diameter change value (i.e., PDC). Maximization was performed using exhaustive search methods, where all possible frequency band choices were considered and the band that provided highest correlation coefficient was selected. Similar maximization is possible using other criteria such as the tRMS differences between the significant and insignificant stenosis. This criterion was also used and resulted in approximately the same frequency values. While the 200-500 Hz band was among the best frequency bands, the correlation coefficient was sufficiently high for other bands. For example, bands that start at 150-300 Hz with a width 100-700 Hz would yield sufficiently high correlations. Further, as the database is expanded after testing more subjects, the system can automatically or manually recalculate optimal frequency bands and better relations between acoustic parameters and percent diameter change.

Figure 18:
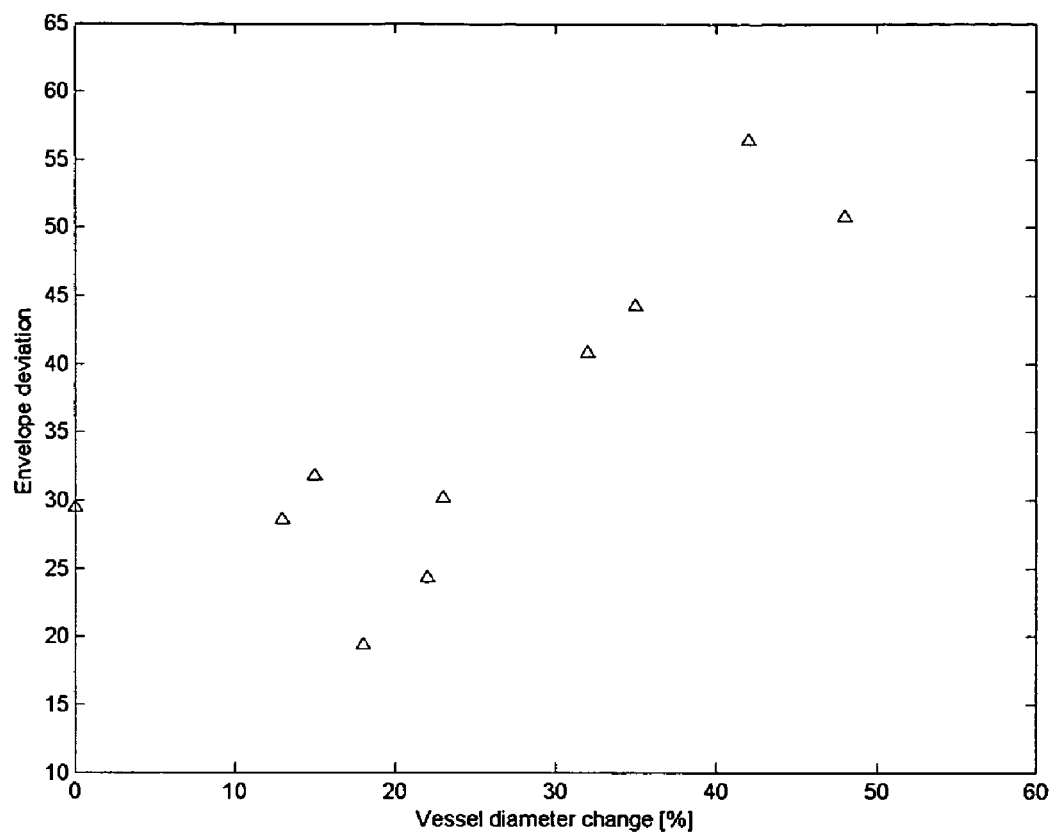
FIG. 18 is an exemplary graphical representation of the RMS of the difference between normalized envelopes associated with stenosed and relieved blood vessel conditions for several subjects exhibiting different degrees of vessel diameter change.

FIG. 18 shows the RMS of the difference of normalized envelopes for a plurality of patients as a function of the change in the percentage of their stenosis. This data shows that the RMS of the differences of the normalized envelopes is indicative of the amount of the percent diameter change, where the relation may be represented using the equation PDC=8+0.6*RMS of difference of normalized envelopes. The procedure to find average signal envelopes is described below in connection with FIG. 19.

Figure 19:
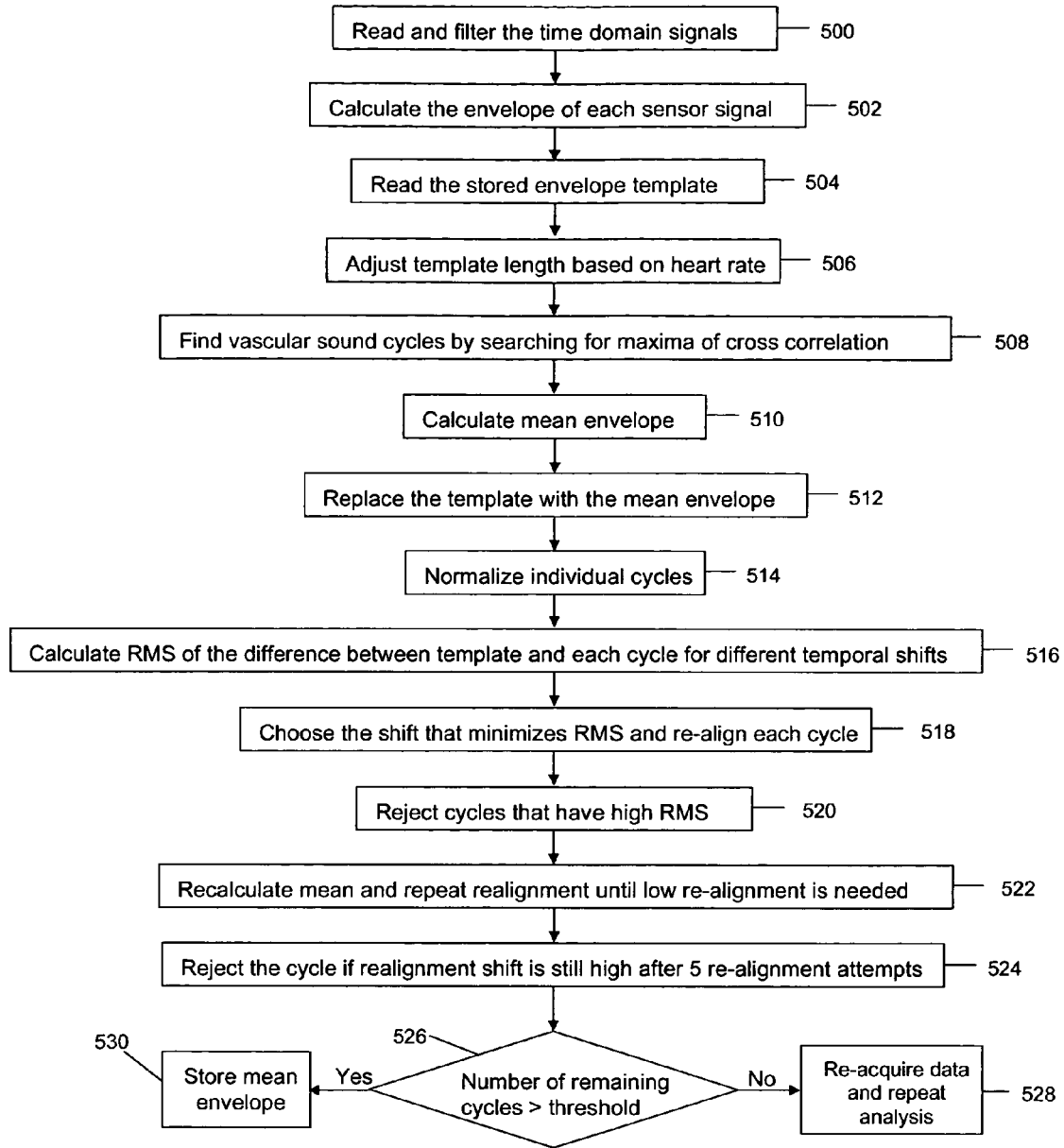
FIG. 19 is an exemplary flow diagram that depicts another manner in which the system of FIG. 2 may be configured to determine the average envelope of a plurality of cardiac cycles.

FIG. 19 is an exemplary flow diagram that illustrates another method by which the apparatus disclosed herein may determine the average envelope of a plurality of cardiac cycles. Block 500 reads and filters a time domain signal using a band-pass filter having, for example, a 100-800 Hz pass band or any other appropriate pass band. Block 502 then calculates the time-dependent signal amplitude or envelope using, for example, the amplitude of the Hilbert transform of the signal. The signal envelope may be smoothed using a 50 ms moving average window. Block 504 reads a stored template of mean or average envelope data that assumes a cardiac cycle length of one second (i.e., a heart rate of 60 cycles/min). The template may, for example, contain 10,000 data points in the case that a sampling frequency of 10 kHz is used. Using actual heart rate, block 506 uses interpolation to correct the number of data points in the template. For example, if the actual heart rate is 120 cycles/minute, block 506 will interpolate the template data to obtain 5,000 data points to represent the envelope template. Block 508 calculates the cross-correlation between the envelope data and the template data and identifies the individual cardiac cycles by searching for the maxima of the cross correlation results. The heart rate used by block 506 may be estimated by the user or determined in any other suitable manner. After identifying the individual cardiac cycles (e.g., from block 508), calculations are preferably repeated starting from block 506 using the correct heart rate (e.g., the heart rate calculated using the timing of identified cardiac cycles). Repeating calculations is particularly useful in cases where the actual heart rate is significantly different from the initial estimated heart rate. After identifying the first cardiac cycle (usually within the first 1-2 seconds of the signal data), block 508 searches for the next correlation maximum. The search for the maximum preferably skips the points (⅓-½ of the cycle period) that are next to the most recent maximum to increase calculation speed. Block 510 calculates the mean cycle envelope by averaging envelopes of all cycles found and replaces the template data with the mean envelope data.

Block 514 normalizes template information and individual cycles (to values ranging from 0 to 1). Block 516 calculates the RMS of the difference between the template information and the data associated with each cardiac cycle. The RMS is calculated while shifting each cycle by different amounts (within, for example, ±one half to one quarter of a period). Block 518 realigns each cycle by selecting a shift that minimizes the RMS of the difference. Block 520 rejects cardiac cycles having an RMS value greater than a threshold value (e.g. >0.1 to 0.2). Block 522 then determines another mean and realigns cycles until realignment changes are less than a threshold (e.g. <1 ms to 5 ms). Block 524 rejects an individual cycle if the realignment shift remains high after several (e.g., more than five) realignment attempts. Block 526 checks if the number of remaining cycles is greater than a minimum (e.g., less than five). If the number of remaining cycles is greater than the minimum, the final mean is stored. Otherwise, block 530 prompts the user to re-acquire the data.

Figure 20:
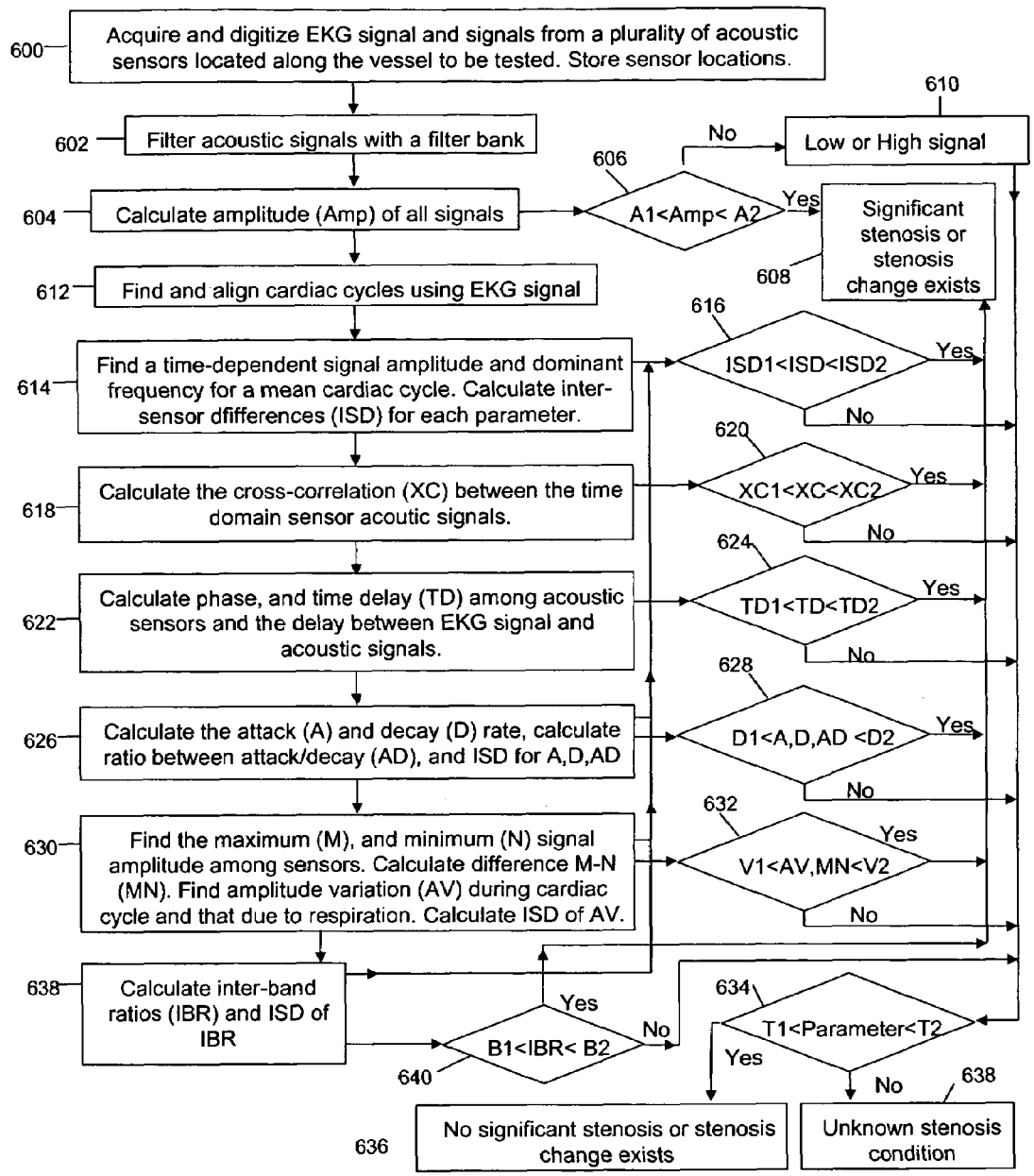
FIG. 20 is an exemplary flow diagram that depicts another manner in which the system of FIG. 2 may be configured to assess bypass grafts and other vascular conditions.

FIG. 20 is an exemplary flow diagram that illustrates one manner in which apparatus in FIG. 2 may be configured to assess bypass grafts and other vessel conditions with or without baseline measurements. In general, the example method depicted in FIG. 20 calculates certain signal characteristics and compares the signal characteristics to predetermined thresholds and/or previous or baseline values. The comparisons of the signal characteristics may be based on comparisons of acoustic characteristics from a plurality of sensors, comparisons among different frequency bands, and comparisons between different phases of cardiac and respiratory cycles. In addition, the comparisons may be performed one at a time or several at a time.

Block 600 acquires and digitizes signals measured from electrocardiography (EKG) leads and acoustic signals from a plurality of sensors located along the vessel to be tested for the presence of stenosis or a change in stenosis. Block 600 also stores the sensor locations, which may be used during the analysis, during serial tests, and/or for future reference. Block 602 decomposes the acoustic signals into a plurality of frequency bands using, for example, one or more filters (e.g., a filter bank). The filter(s) preferably, but do not necessarily, filters acoustic signals using four frequency bands. Specifically, the filter(s) may include a very low frequency band (e.g., <5 Hz), a low frequency band (e.g., 5 Hz to 150 Hz), a midrange frequency band (e.g., 150 Hz to 600 Hz), and a high frequency band (e.g., greater than 600 Hz). The example method depicted in FIG. 20 optimizes the frequency bands used as data is accumulated to maximize the accuracy with which the method can detect vascular stenosis. Block 602 may use Butterworth filters, Chebychev filters, Bessel filters, elliptical filters, or any combination thereof. Other approaches may use multi-resolution wavelet analysis. Alternatively, many of the analyses described below can be performed for each of the frequency bands through the use of well-known auto and cross spectral calculations.

Block 604 calculates the amplitude (Amp) of all acoustic signals. Signal amplitude is perferably calculated using the root-mean-square value. However, other amplitude measures such as maximum value could be used instead of or in addition to the root-mean-square value. Alternatively, the signal energy estimated by the mean-square value can be used. Block 606 determines if at least one acoustic amplitude is higher than a predetermined threshold (A1). If at least one acoustic amplitude is higher than the predetermined threshold A1, then block 608 indicates the presence of stenosis. On the other hand, if no acoustic amplitude is higher than the threshold A1, block 610 reports low or high signal levels to alert the user to check for a malfunction (e.g., due to improperly attached acoustic sensors for low signal levels and extraneous noise for high signal levels). A low level is reported when Amp<A1 and a high signal level is reported when Amp>A2. A typical low signal level occurs at about the limit of human hearing using a regular (non-amplified) stethoscope.

Block 634 determines if signal amplitude (indicated as "Parameter" in the diagram) is within a predetermined range (i.e., between thresholds T1 and T2, where T2 preferably equals A1) before reporting absence of stenosis. A low sound for insignificant stenosis was tested in ten patients, where the sound level was around or below the limit of human hearing using a regular (non-amplified) stethoscope. Low amplitudes also occur for stenoses that exhibit an almost complete blockage. If sound amplitude is outside a certain range (e.g., less than T1), then block 638 reports that the stenosis condition is unknown.

Block 608 can also operate to detect a change in a stenosis state by comparing the current parameter (e.g., Amp) with a previously recorded value (e.g., a baseline value) of the same parameter. Comparison may be performed by calculating the parameter difference and/or the ratio between the new and old value of the parameter and determining if the difference (or ratio) is significantly different from zero (or if the ratio significantly different from one) to indicate a significant change in stenosis. Such comparisons with a baseline value may also be used with other comparisons such as those associated with blocks 616, 620, 624, 628, 632, 634 and 640.

Block 612 finds the acoustic data for each cardiac cycle using the EKG signal. Signals are temporally-aligned and block 614 calculates the mean, the time-dependent amplitude, and dominant frequency during the cardiac cycle. The time dependent signal amplitudes are determined in a manner similar to that used with blocks 114 and 116, where the EKG signal is used as a reference timing signal. Block 614 also compares inter-sensor values by calculating the inter-sensor differences (ISD) of the time-dependent amplitude and dominant frequency. Similar comparisons are also possible using inter-sensor ratios (ISR). Inter-sensor differences or ratios may be calculated among the same or different parts of a cardiac cycle. These inter-sensor differences or ratios are indicative of an emergence or change of vessel stenosis if the differences or ratios fall within predetermined respective ranges. Of course, comparing the ISD amplitude of large parts or different parts of the cycle, or even the whole cycle, are possible.

Block 616 compares ISD and/or ISR in the time-dependent amplitude and dominant frequency to the respective low and high thresholds (ISD1 and ISD2) and reports the existence of stenosis when the condition is met (i.e., within the range defined by the thresholds). If the ISD is outside of the range of stenosis values defined by the thresholds, block 634 compares the ISD to the values associated with a non stenosis range. Of course, the values of thresholds T1, T2, ISD1 and ISD2 may be different for different parameters.

Alignment may be performed using an EKG signal. However, other suitable methods that do not require the EKG signal, such as those used in connection with blocks 106 and 206, can be used instead. Stenosis change can be also determined by comparing the ISD with previously recorded ISD values. Blocks that receive several inputs such as blocks 608 and 634 preferably provide (e.g., display) several outputs, each of which corresponds to an input. Alternatively or additionally, blocks that receive a plurality of inputs may display a single output that combines the effect of all inputs using a neural network or other models well known to those of ordinary skill in the art.

Block 618 calculates the cross-correlation between the time domain signals for each sensor pair. The cross correlation is preferably normalized by dividing the RMS of each signal pair. The maximum cross correlation is designated as XC. A high XC value is indicative of a common sound source for the sensor pair, which in turn is indicative of a dominant sound source of the stenosis. Block 620 compares XC to a threshold value XC1 (typically about 30-50%) and indicates stenosis if XC is greater than the threshold. In this case, the sensors may be spaced, for example, using 2-6 centimeter center-to-center spacing. If the spacing between sensors is too small, XC will tend to be high (event without stenosis) and vice versa. On the other hand, if XC is less than XC1, then XC is checked again in block 634 using XC as the Parameter. Block 636 determines that there is no stenosis if XC is within the thresholds T1 and T2. Preferably, T2 is equal to or less than XC1 and T1 is about 2%. A more reliable value of the cross correlation and XC can found when a high signal-to-noise-ratio portion of the signals is used in these calculations. For example, the loudest half or quarter of the cardiac cycle can be used. Other methods such as calculating the mean coherence (for a certain frequency range) or the correlation coeffiecient of a linear fit between the two signal sets can be used to measure the amount of association between the signals of the sensor pair. In that regard, adaptive filters can be also used to decompose the signal pair into correlated and uncorrelated components that, in turn, can be used to measure the amount of association between each sensor pair signals. Stenosis change can be also determined by comparing XC with previously recorded XC values. The cross correlation and coherence also indicate the time delay between the two signals, which is used in block 622. This time delay may be used to align the two signals and improve the performance of the correlation coefficient of the linear fit.

Block 622 calculates phase and time delay (TD) between acoustic sensor pairs and also between these sensors and the EKG signal. Phase and time delay can be determined using well-known cross-spectrum and auto-spectrum or cross correlation calculations. The presence of stenosis affects flow resistance at the senosis location and the overall blood flow circuit. As a result, stenosis also affects phase and time delay among signal pairs. Block 624 reports the existence of significant stenosis if phase delay falls within certain thresholds (i.e., TD1 and TD2). Otherwise, block 634 reports that no significant stenosis exists if that parameter (i.e., TD) is between thresholds T1 and T2. Of course T1 and T2 corresponding to TD are different from those used for XC as each parameter (i.e., Amp, ISD, XC, TD, . . . , etc) may have its own respective thresholds. Stenosis change can be also determined by comparing TD with previously recorded TD values for the same or other patients.

Block 626 calculates the attack (A) and decay (D) rates, and the ratio between attack and decay (AD). The attack and decay rates are calculated from envelope data of the mean cardiac cycle (block 114) by fitting an exponential curve to the attack and decay parts of the cycle. Other curve fitting such as a straight line or a polynomial fit are also possible. Blocks 628 and 634 compare these parameters (A, D, AD) to the respective thresholds of each for the stenosis (e.g., D1, D2 in block 628) or non-stenosis (i.e., T1 and T2 in block 634) states. The result of these comparisons determines if there is a change in stenosis. Inter sensor differences and/or ratios (of A, D and AD) are also calculated by block 626 and compared to their respective thresholds in blocks 616 and 634.

Block 630 finds the maximum (M) and minimum (N) signal amplitude among sensors preferably for the loudest (or other selected parts of) the cardiac cycle, and compares the maximum to the minimum by calculating a maximum to minimum difference (MN). Other comparisons such as the ratio between maximum and minimum are possible. Finding the inter-sensor maximum and minimum involves localization of amplitude, which may be performed by considering the maximum to be at the point of loudest measurement, or using known array processing methods. Block 630 also finds the amplitude variation (AV) during cardiac cycle and variation due to respiration (AVp) and calculates inter-sensor difference ISD (and/or ratio) of the AV and AVp.

For the amplitude calculations that are performed in the very low frequency range (e.g., at the heart beat rate, which is around 1 Hz), the measured vibrations are indicative of or contain the vessel diameter variation during the cardiac cycle, which contains the combined effects of the pulse pressure (blood pressure variations during the cardiac cycle) and vessel wall elasticity. For example, the increased pulse pressure or wall elasticity increases vessel diameter oscillations during the cycle at low frequencies. This effect is useful in detecting the presence or change in a stenosis because the stenosis increases local vessel resistance to blood flow, which causes the pressure variations downstream of the stenosis to become lower, particularly in comparison to those upstream. Thus, stenosis leads to increased amplitude difference (or ratio) across the stenosis so that the signal amplitude downstream is lower than that upstream (i.e. the downstream to upstream amplitude ratio is lower than unity or the difference is negative). The signal amplitude is further lowered at the stenosis due to wall thickening and reduced vessel wall elasticity.

The situation is different in the middle frequency range (e.g., 150-600 Hz) where most of the turbulent flow sound due to stenosis exists. These sounds are louder downstream of the stenosis where turbulent flow is generated. Thus, the sound amplitude difference between downstream and upstream is positive (i.e., amplitude ratio is greater than unity). This is particularly clear at certain parts of the cardiac cycle, such as the high flow parts. Hence, the increased amplitude downstream of the stenosis is opposite to what was described above for very low frequency vibrations. The combined effects of both phenomena are utilized in block 638.

Block 638 calculates the inter frequency band ratios (IBR, amplitude at high frequency divided by amplitude at low frequency). Downstream of the stenosis the high frequency increases and the low frequency decreases, while the opposite may take place upstream. Thus, the amplitude ratio will increase downstream and decrease upstream. Comparing this ratio upstream and downstream will further help to indicate the presence or change in vessel stenosis. Block 640 compares the IBR to respective thresholds B1 and B2. Similar calculations are also possible among other frequency bands. Block 638 also calculates the inter-sensor difference (ISD) or ratio of IBR. Further, block 616 compares the inter-sensor difference (or ratio) of the inter-band ratio (or difference) by comparing the values to respective thresholds. If the ISD is within the range of stenosis values, block 608 reports the presence of or a change in stenosis, otherwise control is transferred to block 634 and another comparison with thresholds takes place to determine if there is no stenosis, no stenosis change, or if the result is unknown. Inter-band ratios IBR (or differences) of other characteristics (such as XC, TD, A, D, AD, . . . , etc) are also possible. Comparisons can be also made during the same or different parts of the cycle if desired. For example comparisons can be made between different phases of cardiac (e.g. systolic and diastolic, or parts thereof) or respiratory cycles (inspiration and expiration or parts thereof).

After mapping the acoustic field (i.e., defining acoustic characteristics by the parameters calculated in blocks such as 604, 614, 618, 622, 626, 630, and 638), the apparatus and methods can also realign sensors with the stenosis. This can be done by, for example, tracking the maximum sound location or any other acoustic feature. Such alignment can be useful to follow the stenosis location, relocate acoutic sensors or guide ultrasound tests (such as ultrasound imaging or blood flow velocity measurements using doppler ultrasound equipment). Operator guidance can be user interactive or fully automated.

The apparatus and methods described herein may also be used to estimate the transfer function within the body or biological system from sound measurements at different sensor locations while acoustic signals are input form one or more locations. For that purpose one or more sensors will double as a sound input or separate input devices can be used. In some examples, the input signal may be a chirp (sweeping pure tone), maximal length sequence, or band limited white noise. Advantages of using more deterministic signals such as a chirp or maximal length sequences include the relative ease of noise filtering and rejection. Transfer functions between any two points can be calculated through cross-spectral and auto-spectral calculations, or any other known methods. Predictions of spectral alterations and time delay (as a function of distance) from transfer function estimations can then be used to improve system ability to localize sound sources, and correct sounds heard at measurement points.

The example methods and apparatus described herein may also by used to perform self-optimization as more vascular sound data is accumulated. Such self-optimization may update values of thresholds, frequency bands, sensor spacing, and cardiac and respiratory cycle phase. To reduce the effect of ambient noise a microphone is used to measure ambient sounds and then use adaptive filtering to remove that noise.

If implemented in software, the functions and routines discussed herein may be stored in any machine readable media or memory such as on a magnetic, an optical, or other storage medium, in a RAM or ROM of a computer, controller, etc. Likewise, this software may be modulated on a carrier and delivered to a user or a device via any known or desired delivery method including, for example, over a communication channel such as a telephone line, the Internet, etc.

While the invention has been described with reference to specific examples, which are intended to be illustrative only and not to be limiting of the invention, it will be apparent to those of ordinary skill in the art that changes, additions or deletions may be made to the disclosed embodiments without departing from the spirit and the scope of the invention.

What is claimed is:

1. A method of detecting a change in a vascular condition, comprising:

receiving sound information associated with blood flowing through a vascular structure;

converting the sound information into data associated with a plurality of cardiac cycles;

processing the data associated with the plurality of cardiac cycles to determine a spectral characteristic for each of a plurality of frequencies within a frequency band for a first group of the cardiac cycles associated with a current state of the vascular condition and a second group of the cardiac cycles associated with an earlier state of the vascular condition; and detecting the change in the vascular condition based on a comparison between the acoustic characteristic associated with the current state of the vascular condition and an acoustic characteristic associated with the earlier state of the vascular condition, wherein the comparison comprises calculating a difference between each of the spectral characteristics at each of the frequencies for the first group of the cardiac cycles and the spectral characteristic at the corresponding frequency for the second group of the cardiac cycles.

2. A method as defined in claim 1, wherein detecting the change in the vascular condition includes detecting a change in an amount of stenosis associated with the vascular structure.

3. A method as defined in claim 1, wherein detecting the change in the vascular condition includes calculating a parameter associated with a change in a diameter associated with the vascular structure.

4. A method as defined in claim 3, wherein detecting the change in the vascular condition includes comparing the parameter associated with the change in the diameter to a threshold value associated with a significant change in the vascular structure.

5. A method as defined in claim 1, wherein processing the data comprises processing data representing only non-repeatable portions of each of the cardiac cycles.

6. A method as defined in claim 1, wherein the comparison comprises calculating at least one of a true root mean square, a root mean square, or a mean of the differences between each of the spectral characteristics.

7. A method as defined in claim 1, wherein detecting the change in the vascular condition further comprises calculating a difference between first temporal data associated with the acoustic characteristic associated with the earlier state of the vascular condition and second temporal data associated with the acoustic characteristic associated with the current state of the vascular condition.

8. A method as defined in claim 7, wherein calculating the difference between the first temporal data associated with the acoustic characteristic associated with the earlier state of the vascular condition and the second temporal data associated with the acoustic characteristic associated with the current state of the vascular condition includes calculating at least one of a true root mean square, a root mean square, or a mean of the difference between the first and second temporal data.

9. A method as defined in claim 7, wherein the first and second temporal data include signal envelope data.

10. A method as defined in claim 1, wherein receiving the sound information associated with the blood flowing through the vascular structure includes receiving the sound information via a plurality of acoustic sensors proximate to the vascular structure.

11. A method as defined in claim 1, wherein converting the sound information into the data associated with the plurality of cardiac cycles includes using signal envelope template data to temporally align the data associated with the plurality of cardiac cycles.

12. A method as defined in claim 11, wherein using the signal envelope template data to temporally align the data associated with the plurality of cardiac cycles includes identifying each of the cardiac cycles using at least one of maxima information or cross correlation information.

13. A method as defined in claim 11, wherein using the signal envelope template data to temporally align the data associated with the plurality of cardiac cycles includes calculating a difference between the data associated with each of the cardiac cycles and the template data.

14. A method as defined in claim 1, wherein processing the data comprises selecting a band of frequencies that increases a correlation between the acoustic characteristic and the vascular condition.

15. A method as defined in 14, wherein selecting the band of frequencies that increases the correlation between the acoustic characteristic and the vascular condition includes automatically optimizing the band of frequencies.

16. A system for detecting a change in a vascular condition, comprising:
a memory; and
a processor coupled to the memory and programmed to:
receive sound information associated with blood flowing through a vascular structure;
convert the sound information into data associated with a plurality of cardiac cycles;
process the data associated with the plurality of cardiac cycles to determine a spectral characteristic for each of a plurality of frequencies within a frequency band for a first group of the cardiac cycles associated with a current state of the vascular condition and a second group of the cardiac cycles associated with an earlier state of the vascular condition; and
detect the change in the vascular condition based on a comparison between the acoustic characteristic associated with the current state of the vascular condition and an acoustic characteristic associated with the earlier state of the vascular condition, wherein the comparison comprises calculating a difference between each of the spectral characteristics at each of the frequencies for the first group of the cardiac cycles and the spectral characteristic at the corresponding frequency for the second group of the cardiac cycles.

17. A system as defined in claim 16, wherein the processor is programmed to detect the change in the vascular condition by detecting a change in an amount of stenosis associated with the vascular structure.

18. A system as defined in claim 16, wherein the processor is programmed to detect the change in the vascular condition by calculating a parameter associated with a change in a diameter associated with the vascular structure.

19. A system as defined in claim 18, wherein the processor is programmed to detect the change in the vascular condition by comparing the parameter associated with the change in the diameter to a threshold value associated with a significant change in the vascular structure.

20. A system as defined in claim 16, wherein the processor is programmed to process the data by processing data representing only non-repeatable portions of each of the cardiac cycles.

21. A system as defined in claim 16, wherein the comparison comprises calculating at least one of a true root mean square, a root mean square, or a mean of the differences between each of the spectral characteristics.

22. A system as defined in claim 16, wherein the processor is programmed to detect the change in the vascular condition by calculating a difference between first temporal data associated with the acoustic characteristic associated with the earlier state of the vascular condition and second temporal data associated with the acoustic characteristic associated with the current state of the vascular condition.

23. A system as defined in claim 22, wherein the processor is programmed to calculate the difference between the first temporal data associated with the acoustic characteristic associated with the earlier state of the vascular condition and the second temporal data associated with the acoustic characteristic associated with the current state of the vascular condition by calculating at least one of a true root mean square, a root mean square, or a mean of the difference between the first and second temporal data.

24. A system as defined in claim 22, wherein the first and second temporal data include signal envelope data.

25. A system as defined in claim 16, wherein the processor is programmed to receive the sound information associated with the blood flowing through the vascular structure via a plurality of acoustic sensors proximate to the vascular structure.

26. A system as defined in claim 16, wherein the processor is programmed to convert the sound information into the data associated with the plurality of cardiac cycles using signal envelope template data to temporally align the data associated with the plurality of cardiac cycles.

27. A system as defined in claim 26, wherein the processor is programmed to use the signal envelope template data to temporally align the data associated with the plurality of cardiac cycles by identifying each of the cardiac cycles using at least one of maxima information or cross correlation information.

28. A system as defined in claim 26, wherein the processor is programmed to use the signal envelope template data to temporally align the data associated with the plurality of cardiac cycles by calculating a difference between the data associated with each of the cardiac cycles and the template data.

29. A system as defined in claim 16, wherein the processor is programmed to process the data by selecting a band of frequencies that increases a correlation between the acoustic characteristic and the vascular condition.

30. A method as defined in 29, wherein the processor is programmed to select the band of frequencies that increases the correlation between the acoustic characteristic and the vascular condition includes by automatically optimizing the band of frequencies.

31. A machine readable medium having instructions stored thereon that, when executed, cause a machine to:
receive sound information associated with blood flowing through a vascular structure;
convert the sound information into data associated with a plurality of cardiac cycles;
process the data associated with the plurality of cardiac cycles to determine a spectral characteristic for each of a plurality of frequencies within a frequency band for a first group of the cardiac cycles associated with a current state of the vascular condition and a second group of the cardiac cycles associated with an earlier state of the vascular condition; and
detect a change in the vascular condition based on a comparison between the acoustic characteristic associated with the current state of the vascular condition and an acoustic characteristic associated with the earlier state of the vascular condition, wherein the comparison comprises calculating a difference between each of the spectral characteristics at each of the frequencies for the first group of the cardiac cycles and the spectral characteristic at the corresponding frequency for the second group of the cardiac cycles.

32. A machine readable medium as defined in claim 31 having instructions stored thereon that, when executed, cause the machine to detect the change in the vascular condition by detecting a change in an amount of stenosis associated with the vascular structure.

33. A machine readable medium as defined in claim 31 having instructions stored thereon that, when executed, cause the machine to detect the change in the vascular condition by calculating a parameter associated with a change in a diameter associated with the vascular structure.

34. A machine readable medium as defined in claim 33 having instructions stored thereon that, when executed, cause the machine to detect the change in the vascular condition by comparing the parameter associated with the change in the diameter to a threshold value associated with a significant change in the vascular structure.

35. A machine readable medium as defined in claim 31 having instructions stored thereon that, when executed, cause the machine to process the data by processing data representing only non-repeatable portions of each of the cardiac cycles.

36. A machine readable medium as defined in claim 31 wherein the comparison comprises calculating at least one of a true root mean square, a root mean square, or a mean of the differences between each of the spectral characteristics.

37. A machine readable medium as defined in claim 31 having instructions stored thereon that, when executed, cause the machine to detect the change in the vascular condition by calculating a difference between first temporal data associated with the acoustic characteristic associated with the earlier state of the vascular condition and second temporal data associated with the acoustic characteristic associated with the current state of the vascular condition.

38. A machine readable medium as defined in claim 37 having instructions stored thereon that, when executed, cause the machine to calculate the difference between the first temporal data associated with the acoustic characteristic associated with the earlier state of the vascular condition and the second temporal data associated with the acoustic characteristic associated with the current state of the vascular condition by calculating at least one of a true root mean square, a root mean square, or a mean of the difference between the first and second temporal data.

39. A machine readable medium as defined in claim 37, wherein the first and second temporal data include signal envelope data.

40. A machine readable medium as defined in claim 31 having instructions stored thereon that, when executed, cause the machine to receive the sound information associated with the blood flowing through the vascular structure includes receiving the sound information via a plurality of acoustic sensors proximate to the vascular structure.

41. A machine readable medium as defined in claim 31 having instructions stored thereon that, when executed, cause the machine to convert the sound information into the data associated with the plurality of cardiac cycles using signal envelope template data to temporally align the data associated with the plurality of cardiac cycles.

42. A machine readable medium as defined in claim 41 having instructions stored thereon that, when executed, cause the machine to use the signal envelope template data to temporally align the data associated with the plurality of cardiac cycles by identifying each of the cardiac cycles using at least one of maxima information or cross correlation information.

43. A machine readable medium as defined in claim 41 having instructions stored thereon that, when executed, cause the machine to use the signal envelope template data to temporally align the data associated with the plurality of cardiac cycles by calculating a difference between the data associated with each of the cardiac cycles and the template data.

44. A machine readable medium as defined in claim 31, wherein the instructions, when executed, cause the machine to process the data by selecting a band of frequencies that increases a correlation between the acoustic characteristic and the vascular condition.

45. A machine readable medium as defined in 44, wherein the instructions, when executed, cause the machine to select the band of frequencies that increase the correlation between the acoustic characteristic and the vascular condition by automatically optimizing the band of frequencies.

* * * * *